US009592024B2

(12) United States Patent
Iizuka et al.

(10) Patent No.: US 9,592,024 B2
(45) Date of Patent: Mar. 14, 2017

(54) MEDICAL IMAGING APPARATUS AND BED FOR MEDICAL IMAGING APPARATUS

(71) Applicant: HITACHI, LTD., Tokyo (JP)

(72) Inventors: Satoshi Iizuka, Tokyo (JP); Izumi Sunazuka, Tokyo (JP)

(73) Assignee: HITACHI, LTD., Tokyo (JP)

( * ) Notice: Subject to any disclaimer, the term of this patent is extended or adjusted under 35 U.S.C. 154(b) by 402 days.

(21) Appl. No.: 14/353,964

(22) PCT Filed: Nov. 14, 2012

(86) PCT No.: PCT/JP2012/079460
§ 371 (c)(1),
(2) Date: Apr. 24, 2014

(87) PCT Pub. No.: WO2013/073550
PCT Pub. Date: May 23, 2013

(65) Prior Publication Data
US 2014/0296692 A1 Oct. 2, 2014

(30) Foreign Application Priority Data

Nov. 18, 2011 (JP) ................................ 2011-252297

(51) Int. Cl.
*A61B 6/00* (2006.01)
*A61B 6/04* (2006.01)
(Continued)

(52) U.S. Cl.
CPC ............ *A61B 6/566* (2013.01); *A61B 5/0555* (2013.01); *A61B 6/032* (2013.01); *A61B 6/035* (2013.01);
(Continued)

(58) Field of Classification Search
CPC ......... A61B 5/0555; A61B 6/032; A61B 6/04; A61B 6/0407; A61B 6/0457; A61B 6/56;
(Continued)

(56) References Cited

U.S. PATENT DOCUMENTS 4,727,328 A * 2/1988 Carper ................. A61B 6/0442
324/318
5,525,905 A * 6/1996 Mohapatra ........... A61B 6/0457
324/318
(Continued)

FOREIGN PATENT DOCUMENTS

| JP | 8-206104 | 8/1996 |
|---|---|---|
| JP | 2005-508691 | 4/2005 |
| JP | 2006-507868 | 3/2006 |

OTHER PUBLICATIONS

International Search Report in PCT/JP2012/079460.

*Primary Examiner* — Robert G Santos
*Assistant Examiner* — David R Hare
(74) *Attorney, Agent, or Firm* — Cooper & Dunham LLP

(57) ABSTRACT

Provided is a medical imaging apparatus that, while preventing damage of connector pins, can simultaneously connect electric connectors when a bed is mechanically docked with an apparatus main body. One coupling mechanism either on an apparatus main body side or on a bed side includes a coupling plate, and the other coupling mechanism includes a holding member that holds a coupling plate that, during coupling, respectively contacts both side surfaces of the coupling plate at two or more points, and sandwiches and holds the coupling plate from both sides. A first electric connector is mounted on the coupling plate, a second electric connector is mounted on the holding member, and an electric connector coupling mechanism that couples the first and second electric connectors is mounted on at least one of the (Continued)

coupling plate and the holding member in a state where the coupling plate is held by the holding member.

13 Claims, 39 Drawing Sheets

(51) Int. Cl.
 *A61B 5/055* (2006.01)
 *A61B 6/03* (2006.01)
(52) U.S. Cl.
 CPC .......... *A61B 6/0407* (2013.01); *A61B 6/0457* (2013.01); *A61B 6/4411* (2013.01); *A61B 6/56* (2013.01); *A61B 6/467* (2013.01)
(58) Field of Classification Search
 CPC ....... A61B 6/035; A61B 6/566; A61B 6/4411; A61B 6/467
 See application file for complete search history.

(56) References Cited

U.S. PATENT DOCUMENTS

| | | | |
|---|---|---|---|
| 6,776,527 B1* | 8/2004 | Tybinkowski | A61B 6/04 378/195 |
| 9,248,067 B2* | 2/2016 | Sunazuka | A61B 5/0555 |
| 2005/0020906 A1* | 1/2005 | Seijger | A61B 6/0457 600/415 |
| 2005/0034237 A1* | 2/2005 | Lenting | A61B 6/0457 5/600 |
| 2006/0167356 A1* | 7/2006 | Everett | A61B 6/0457 600/407 |
| 2014/0303477 A1* | 10/2014 | Sunazuka | A61B 5/0555 600/407 |
| 2014/0357981 A1* | 12/2014 | Dumoulin | A61B 5/0555 600/415 |

* cited by examiner

MEDICAL IMAGING APPARATUS AND BED FOR MEDICAL IMAGING APPARATUS

TECHNICAL FIELD

The present invention relates to a medical imaging apparatus, and particularly, to a bed that is attachable to and detachable from an apparatus main body.

BACKGROUND ART

Medical imaging apparatuses, such as a magnetic resonance imaging (hereinafter referred to as an MRI) apparatus and a CT apparatus, have a structure in which an object is mounted on a bed and the bed is inserted into an imaging space of an apparatus main body. Therefore, the bed has a complicated configuration including a lifting mechanism that lifts a top plate, on which the object is mounted, to the height of the imaging space of the apparatus main body, a horizontal movement mechanism that horizontally moves the top plate in order to insert an imaging site of the object up to the center of the imaging space, a control unit that performs the movement according to a control signal from the apparatus main body, or the like. For this reason, the bed usually has a weight of hundreds of kilograms, is precisely positioned, and is mechanically and electrically connected to the apparatus main body.

In recent years, for an improvement in the throughput of examination for objects, beds that are usable after being separated from the apparatus main body are required.

For example, in the case of an object that cannot enter a bed by itself, the work of transporting the object to the vicinity of the bed, lifting the object by two or more examiners, and mounting and fixing the object to the bed is required, and examiner's burden is great. Particularly in the case of an MRI apparatus, metallic mobile beds, such as a usual stretcher, are drawn close to the apparatus main body by a strong magnetic field generated from the apparatus main body. Therefore, the object cannot be transported to the side of a bed fixed to the MRI apparatus by the usual mobile beds.

Therefore, in the related art, an object is transported in a procedure of transferring the object from the usual stretcher to a special stretcher made of a nonmagnetic substance in the lobby of an examination room, and transporting the object to the side of the bed of the MRI apparatus. In this case, a transfer from a bed to the usual stretcher, a transfer from the usual stretcher to the nonmagnetic stretcher, and a transfer from the nonmagnetic stretcher to the bed of the MRI apparatus are required, and the number of transfer times is three.

Therefore, if the bed of the MRI apparatus can be separated from the main body and be pushed with the hands and moved to the lobby of the examination room or the bedside of an object, and the object can be directly transferred from the usual stretcher or bed to the bed of the MRI apparatus, the number of times of transfer can be reduced. Accordingly, not only can an improvement in the throughput of examination be realized, but also a burden to the object can be reduced.

A bed that is attachable to and detachable from a main body of an MRI apparatus is disclosed in PTL 1. In this technique, as shown in FIGS. 1 to 5 of PTL 1, a front lower portion of the apparatus main body is equipped with a docking mechanism 16, such as a guide 24 having a conical outer shape. Meanwhile, a lower portion of a front end of a bed is equipped with a coupling mechanism to be coupled to the docking mechanism 16. When the bed is coupled to the apparatus main body, the bed is brought close to the apparatus main body until a lateral plate 100 arranged at a front end portion of the bed bumps against docking points 32 and 34 on both sides of an upper portion of the conical guide 24 of the apparatus main body.

The movement of the bed at this time is guided as a pair of pins 96 and 98 below the lateral plate 100 are inserted so as to run along the conical guide 24 of the apparatus main body. If the lateral plate 100 of the bed bumps against the docking point 32, the bed is fixed to the apparatus main body by coupling a latch hook 58 of a lower portion of the bed to a pin member 56 at the tip of the conical guide 24 of the apparatus main body.

CITATION LIST

Patent Literature

[PTL 1] Specification of U.S. Pat. No. 4,567,894

SUMMARY OF INVENTION

Technical Problem

As described above, the bed moves the imaging site of the object to the center of the imaging space under the control of a control device of the medical imaging apparatus. For this reason, when the bed that is movable after being separated from the apparatus main body is docked with the apparatus main body, it is necessary not only to mechanically couple the bed to the apparatus main body, but also to electrically connect a plurality of signal lines of the bed to a plurality of signal lines of the main body.

Since the docking mechanism described in PTL 1 is a docking mechanism that performs mechanical docking, electrical docking cannot be performed by the mechanism of PTL 1. Usually, the electrical docking is performed by means such as inserting connectors with the hands, and user-friendliness is low. Since the number of the signal lines that couple the apparatus main body of the MRI apparatus and the bed are several tens or more and the number thereof is large, large-sized connectors are required in order to couple these lines using the connectors. Since the large-sized connectors require a force when being connected by the hands and are limited in terms of a space where the connector can be arranged, connection operation becomes difficult.

Therefore, it is possible to adopt a configuration in which the connectors are mechanistically connected. For example, it is considered that a mechanism moving the connectors for coupling therebetween is arranged around the connectors, and the connectors are coupled together face to face through the operation of this mechanism. However, when the mechanism is operated in a state where a connector on a bed side and a connector on an apparatus main body side have positionally deviated, there is a risk that the connectors may collide with each other and damage the connector pins, in a state where the connectors have positionally deviated.

An object of the invention is to provide a medical imaging apparatus that, while preventing damage of connector pins, can simultaneously connect electric connectors when a bed is mechanically docked with an apparatus main body.

Solution to Problem

In order to achieve the above object, a medical imaging apparatus of the invention has an apparatus main body equipped with an imaging function of an object, a movable bed, and coupling mechanisms respectively arranged on an apparatus main body side and a bed side in order to detachably couple the bed to the apparatus main body. One coupling mechanism either on the apparatus main body side or on the bed side includes a coupling plate, and the other coupling mechanism includes a holding member that, during coupling, holds the coupling plate. A first electric connector is mounted on the coupling plate, and a second electric connector is mounted on the holding member. An electric connector coupling mechanism that couples the first and second electric connectors is mounted on at least one of the coupling plate and the holding member in a state where the coupling plate is held by the holding member.

Advantageous Effects of Invention

According to the invention, the electric connectors can also be connected simultaneously when the bed is mechanically docked with the apparatus main body, and damage of the connector pins can also be prevented.

DESCRIPTION OF EMBODIMENTS

Figure 1:
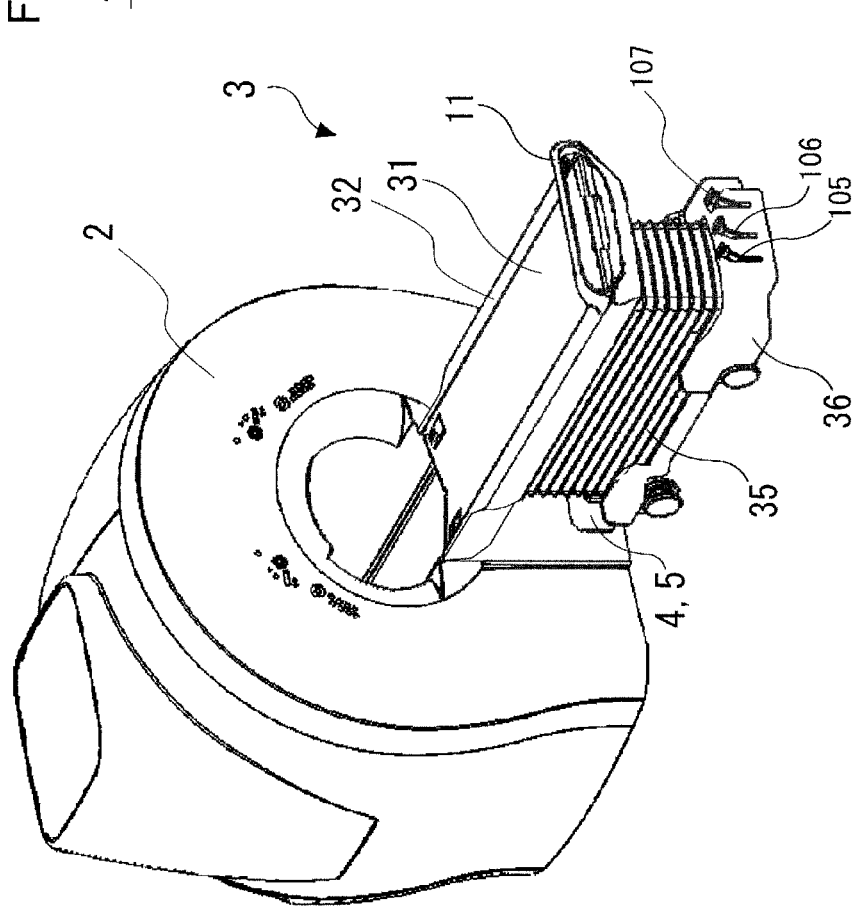
FIG. 1 is a perspective view of a medical imaging apparatus of the present embodiments.

A medical imaging apparatus of the invention has an apparatus main body equipped with an imaging function of an object, a movable bed, and coupling mechanisms arranged on an apparatus main body side and a bed side, respectively, in order to detachably couple the bed to the apparatus main body. One coupling mechanism either on the apparatus main body side or on the bed side includes a coupling plate, and the other coupling mechanism includes a holding member that, during coupling, respectively contacts both side surfaces of the coupling plate at two or more points and sandwiches and holds the coupling plate from both sides. A first electric connector is mounted on the coupling plate, and a second electric connector is mounted on the holding member. An electric connector coupling mechanism that couples the first and second electric connectors is mounted on at least one of the coupling plate and the holding member in a state where the coupling plate is held by the holding member.

The electric connector coupling mechanism is configured to include, as an example, a hook-shaped coupling tool attached to one of the first and second electric connectors, and a pin attached to the other. As the coupling tool is engaged with the pin, the first and second electric connectors are coupled.

The electric connector coupling mechanism may be configured to include a sliding mechanism that slidably holds one of the first and second electric connectors in a direction approaching the other when the coupling tool is engaged with the pin.

Additionally, the electric connector coupling mechanism may be configured to include a biasing member that biases one of the first and second electric connectors in a direction along the sliding mechanism away from the other when the coupling tool is disengaged from the pin.

It is desirable that the electric connector coupling mechanism include a movable mechanism that displaces one of the first and second electric connectors to the other so as to align the first and second electric connectors with each other.

For example, the movable mechanism is configured to include an elastic member that supports one of the first and second electric connectors so as to be displaceable in directions of two or more dimensions with respect to the other.

Additionally, it is possible to adopt a configuration in which the movable mechanism includes one or more sliding plates and the elastic member supports the one or more sliding plates. The electric connectors are configured so as to be supported by a front surface of a first sliding plate of the sliding plates. In this case, for example, it is possible to adopt a configuration in which the first sliding plate is supported by the elastic member from vertical and horizontal directions, and the second sliding plate arranged so as to contact a rear surface of the first sliding plate is supported by the elastic member so as to be pushed out from the rear surface to the front by the elastic member.

Additionally, a configuration may be adopted in which the movable mechanism includes a ball joint and the elastic member supports the ball joint.

One or more locating pins may be formed on one facing surface of the first and second electric connectors so as to protrude toward the other facing surface, and holes having the locating pins inserted thereinto may be provided in the other facing surface.

For example, when two or more locating pins are provided, the lengths thereof are made different. In this case, it is preferable that the diameter of a tip of a long pin among the locating pins be smaller than the diameter of a base of the pin.

It is possible to make a design in which the first and second electric connectors are mounted on the coupling plate and the holding member so as to face each other with a predetermined spacing in a state where the coupling plate is held by the holding member. In this case, it is preferable that a long pin among the locating pins be longer than the predetermined spacing, and a short pin be shorter than the predetermined spacing.

It is possible to adopt a configuration in which the coupling tool includes a first arm that rotates the coupling tool in a direction in which the coupling tool is engaged with the pin, and a second arm that rotates the coupling tool in a direction in which the coupling tool is decoupled from the pin.

In this case, one end of a first wire is connected to the first arm, and one end of a second wire is connected to the second arm. The other ends of the first and second wires are connected to first and second operating units, respectively.

A guide mechanism that is displaced by the second wire while being guided in a movement direction of the second arm may be arranged at the second arm between the second arm and the second wire.

For example, the coupling plate is fixed so as to protrude toward the apparatus main body along a long-axis direction of the bed.

It is possible to adopt a configuration in which both sides of the coupling plate are linear, and the holding member contacts and respectively holds both side surfaces of the linear coupling plate at two or more points.

It is preferable that the coupling plate have a substantially trapezoidal shape in which the width of the plate on the apparatus main body side is smaller than the width of a base of the plate fixed to the bed.

It is also possible to further include a mechanism that connects the coupling plate to the coupling mechanism on a holding member side with the hook.

It is also possible to adopt a configuration in which the coupling mechanism including the holding member has a guide member that guides the coupling plate so as to be led between the guide member and the holding member.

Hereinafter, embodiments of the invention will be specifically described with reference to the drawings.

A medical imaging apparatus 1, as shown in FIG. 1, includes an apparatus main body 2 and a bed 3. The apparatus main body 2 may have any configuration as long as an image of an object mounted on the bed 3 may be captured. For example, a main body of an MRI apparatus or a CT apparatus can be used. Here, a case where the medical imaging apparatus 1 is the MRI apparatus will be described below as an example.

The apparatus main body 2 is configured to include a gantry equipped with a static magnetic field generator that generates a static magnetic field, a gradient magnetic field coil, a radio frequency (RE) magnetic field pulse transmitting coil, and a shim plate and a gantry cover that covers the gantry. In the example of FIG. 1, the static magnetic field generator of the gantry is in the shape of a cylinder in which an axial direction is made horizontal, and the internal space of the cylinder serves as an imaging space. However, the invention is not limited to the cylindrical static magnetic field generator.

Moreover, the MRI apparatus includes a gradient magnetic field power amplifier that supplies an electric current to the gradient magnetic field coil, a radio frequency power amplifier that supplies a radio frequency signal to the RF magnetic field pulse transmitting coil, a radio frequency amplifying circuit, a computer, an operating unit, and a display, as a power source, control, and signal processing system.

The apparatus main body 2 is arranged in an electromagnetically shielded room, and the power source, control, and signal processing system is arranged outside the electromagnetically shielded room, and is electrically connected to the apparatus main body with a cable.

The static magnetic field generator generates a static magnetic field in the imaging space, and the shim plate generates a magnetic field that improves the uniformity of the static magnetic field to a predetermined value or higher. The gradient magnetic field coil generates gradient magnetic fields in predetermined XYZ directions, respectively, in the imaging space. The RF magnetic field pulse transmitting coil transmits an RE magnetic field pulse to the imaging space.

The computer outputs control signals to the gradient magnetic field power amplifier, the radio frequency power amplifier, and the radio frequency amplifying circuit, and controls the application timing and direction of a gradient magnetic field, the irradiation timing of an RF magnetic field pulse, or the like according to a predetermined imaging sequence. Accordingly, the nuclear magnetic-resonance (NMR) signal produced from an object is received by a receiving coil arranged near the object. The radio frequency amplifying circuit detects and amplifies this signal under the control of the computer, and the computer reconstructs an image according to a predetermined image reconstruction program, and displays the image on a display or the like. The operating unit receives imaging conditions or the like from an examiner.

The bed 3 includes a top plate 31 that allows an object to be mounted thereon, a top plate holding portion 32 that holds the top plate 31, a frame that holds the top plate holding portion 32 so as to be vertically movable, a vertical drive unit that vertically moves the top plate holding portion 32, a horizontal drive mechanism that horizontally moves the top plate 31 with respect to the top plate holding portion 32, a horizontal drive unit that drives the horizontal drive mechanism, four wheels 33 that are attached to a lower portion of the frame, bellows portions 35 and a cover 36 that cover an outer periphery of the frame, and a handle portion 11. By virtue of these configurations, the bed 3 can be inserted into an imaging region by raising the top plate 31 to the height of the imaging space of the gantry of the apparatus main body 2 and making the top plate 31 slide horizontally with respect to the top plate holding portion 32. This allows an imaging site of an object to be transported to the center of the imaging space.

Figure 2:
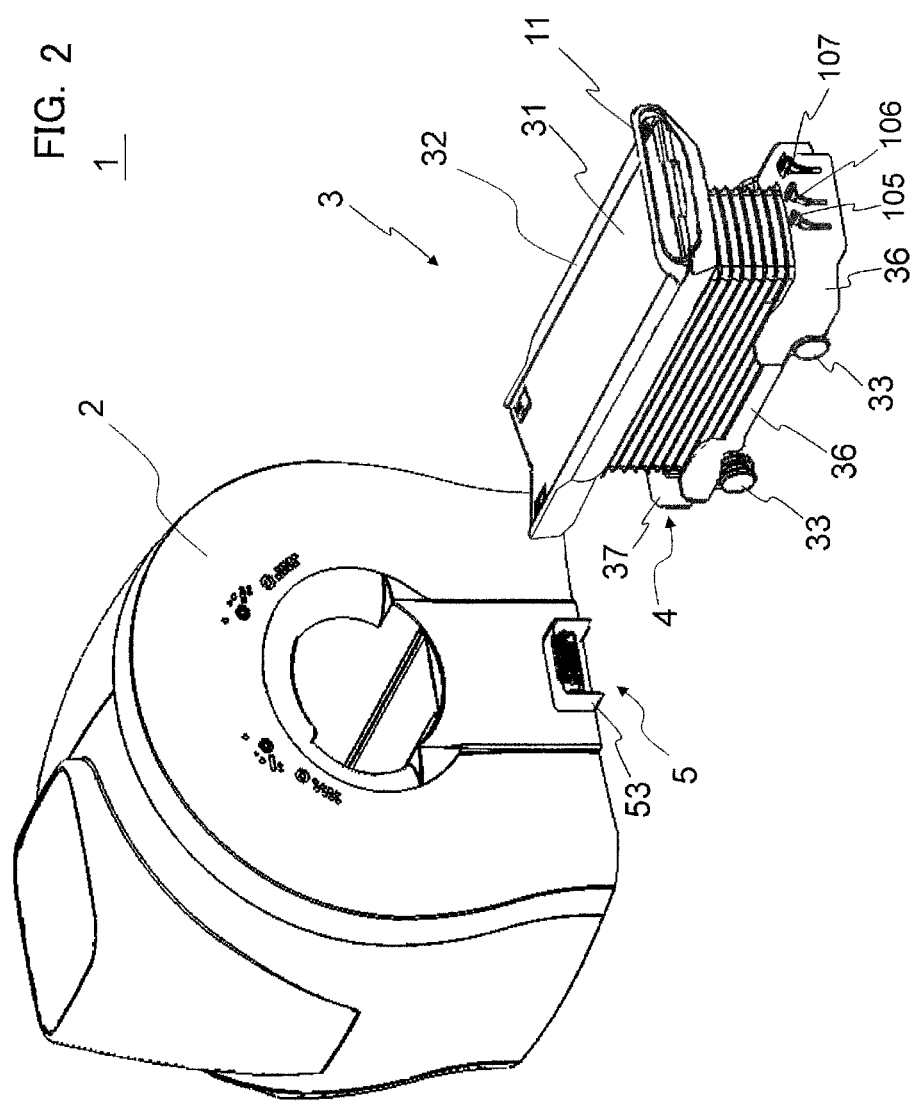
FIG. 2 is a perspective view of the state of the medical imaging apparatus of FIG. 1 where a bed 3 is separated from an apparatus main body 2.

In the invention, the bed 3 is attachable to and detachable from the apparatus main body 2. An object can be mounted on the bed by pushing the handle portion 11 of the bed 3 separated from the apparatus main body 2 as shown in FIG. 2 with his/her hands and moving the bed to a lobby, a hospital room of the object, or the like where the magnetism of the apparatus main body 2 does not reach. After the mounting, the bed can be docked with the apparatus main body 2 as shown in FIG. 1 in a state where the object is mounted.

A front end portion of the bed 3 and a front surface of the apparatus main body 2 are respectively equipped with docking units 4 and 5 as the coupling mechanisms. As the docking units 4 and 5 are fitted to each other, the bed 3 is mechanically coupled to the apparatus main body 2. Additionally, the electric connectors and mechanism units thereof are respectively arranged within the docking units 4 and 5. After the docking units 1 and 5 are mechanically coupled, the electric connector within the docking unit 4 is coupled to and is electrically connected to the electric connector within the docking unit 5 through the operation of the mechanism units of the electric connectors.

Three pedals 105, 106, and 107 are installed at a rear side end portion of the bed 3. The pedal 105 is a pedal for performing the operation of coupling the hook in the docking unit 4 to the coupling bar within the docking unit 5 to complete mechanical docking after the docking units 4 and 5 are fitted to each other. The pedal 106 is a pedal for performing the operation of coupling the electric connectors arranged within the docking unit 4 and 5, respectively, after the completion of the mechanical docking. The pedal 107 is a pedal for releasing the coupling of the electric connectors and the mechanical docking in this order.

<First Embodiment>

The structure of the docking units 4 and 5 will be specifically described with reference to FIG. 3 or the like.

Figure 3:
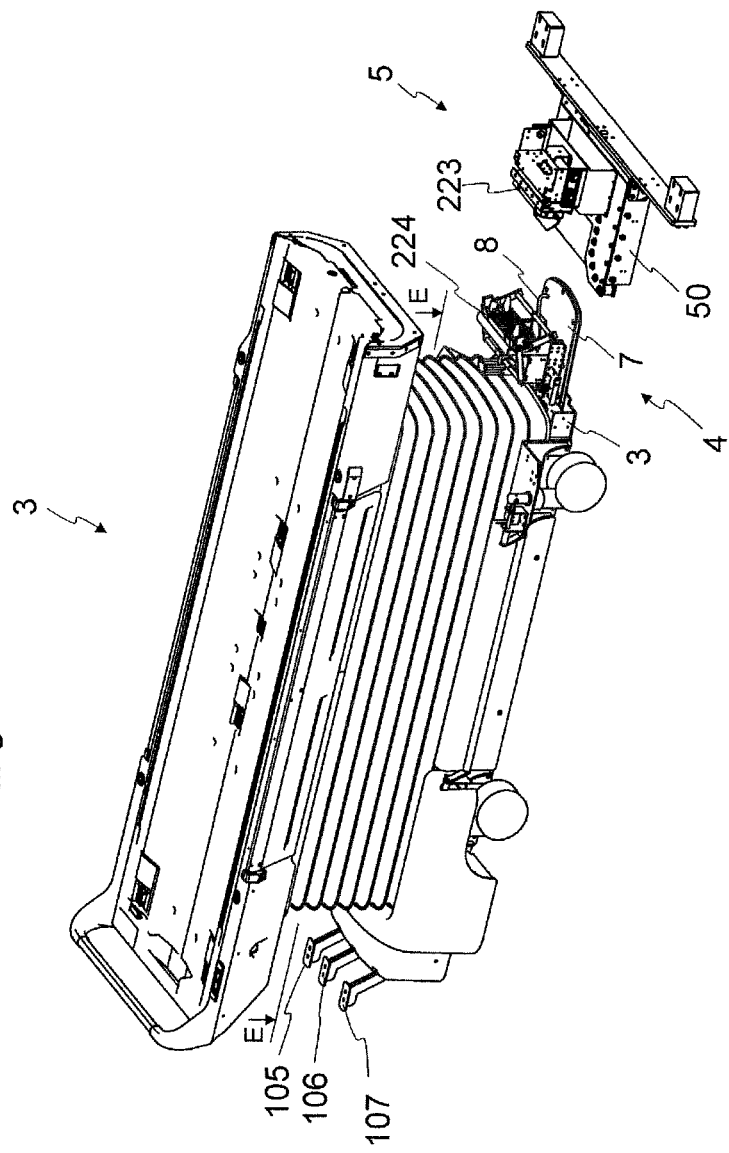
FIG. 3 is a perspective view of the state of the medical imaging apparatus of FIG. 1 where the bed 3 is separated from the apparatus main body 2 and covers are removed from docking units 4 and 5.
Figure 4:
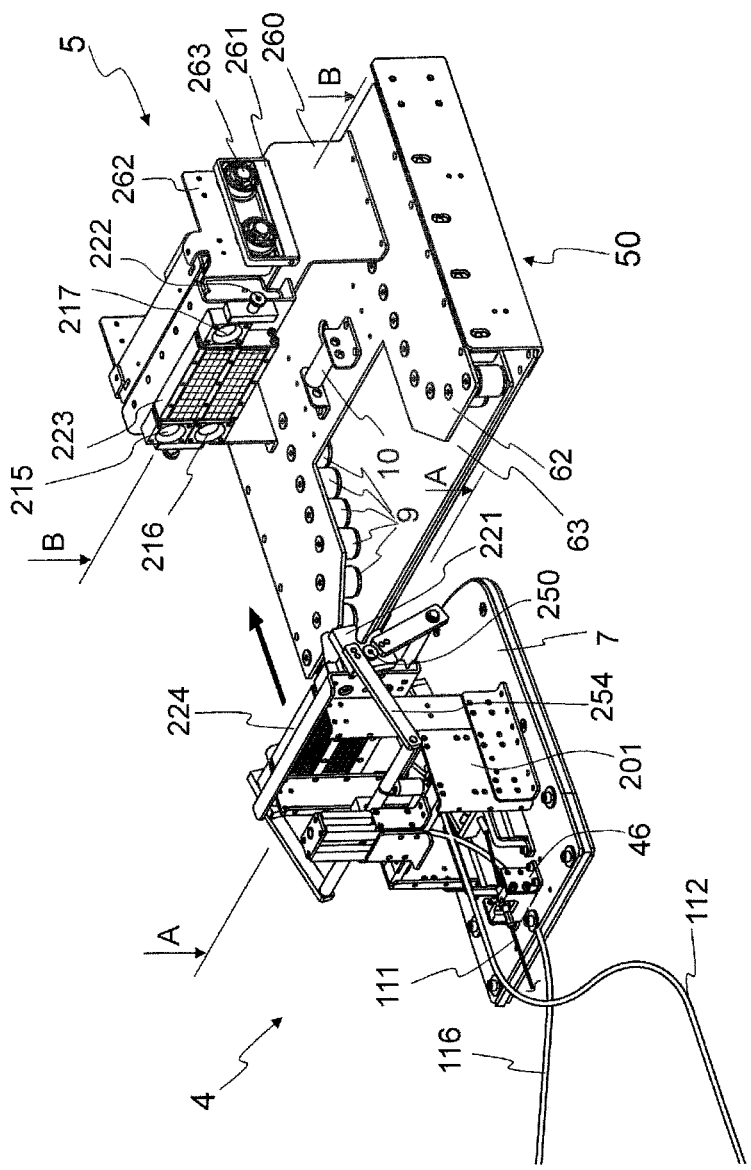
FIG. 4 is an enlarged perspective view of the state of the medical imaging apparatus of FIG. 1 where the covers are removed from the docking units 4 and 5.
Figure 5:
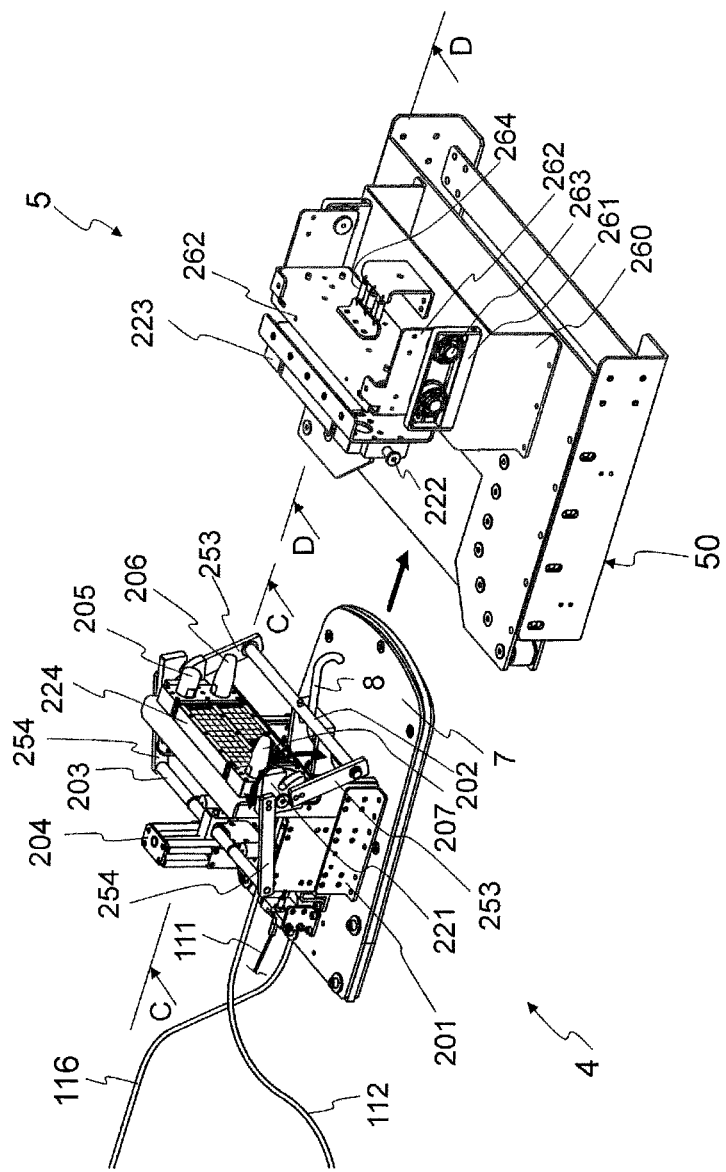
FIG. 5 is an enlarged perspective view of the state of the medical imaging apparatus of FIG. 1 where the covers are removed from the docking units 4 and 5.
Figure 6:
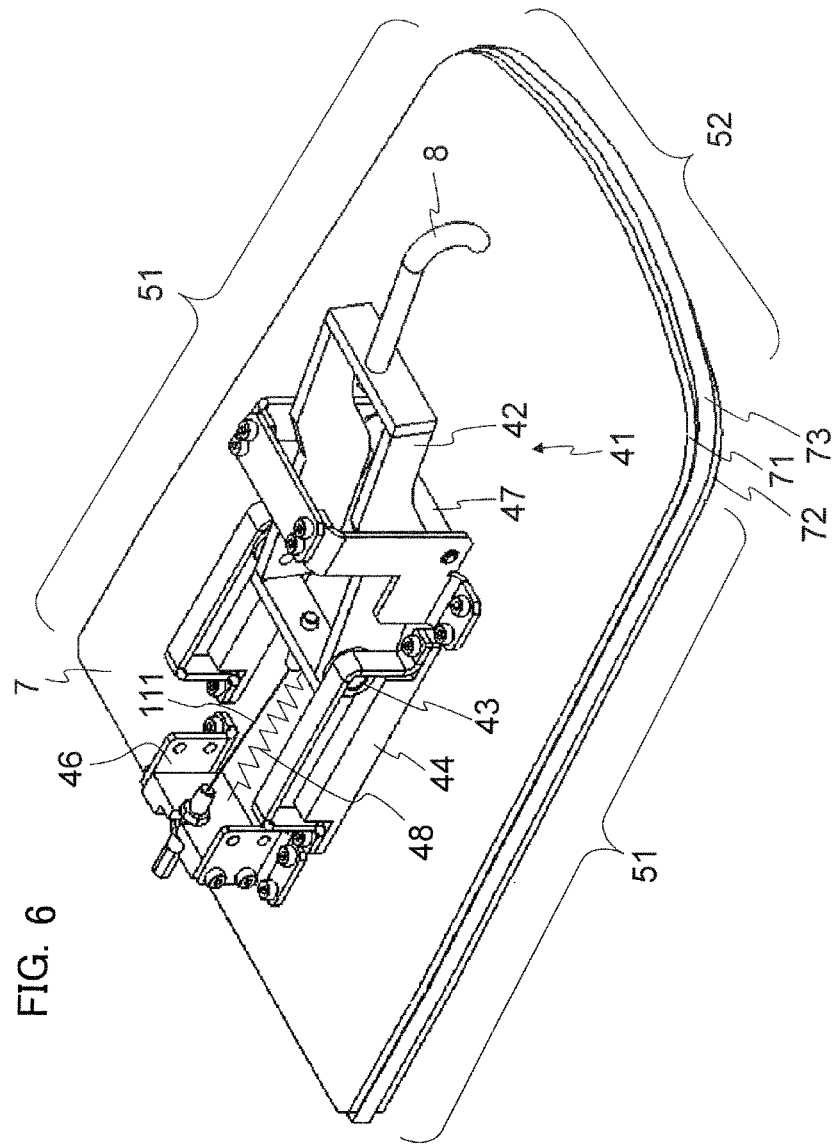
FIG. 6 is an enlarged perspective view of the state of the medical imaging apparatus of FIG. 1 where the cover and an electric connector are removed from docking unit 4.
Figure 7:
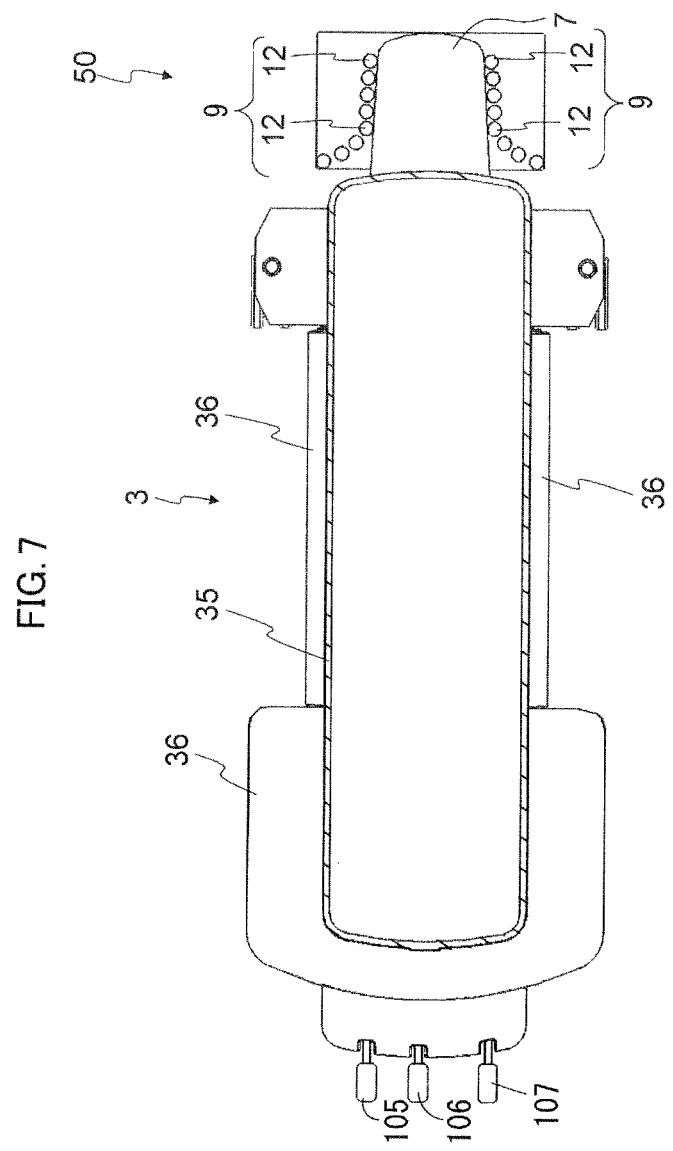
FIG. 7 is a cross-sectional view, taken along E-E of FIG. 3, of the bed 3 and the roller unit 50 in a coupled state, in a first embodiment.
Figure 8:
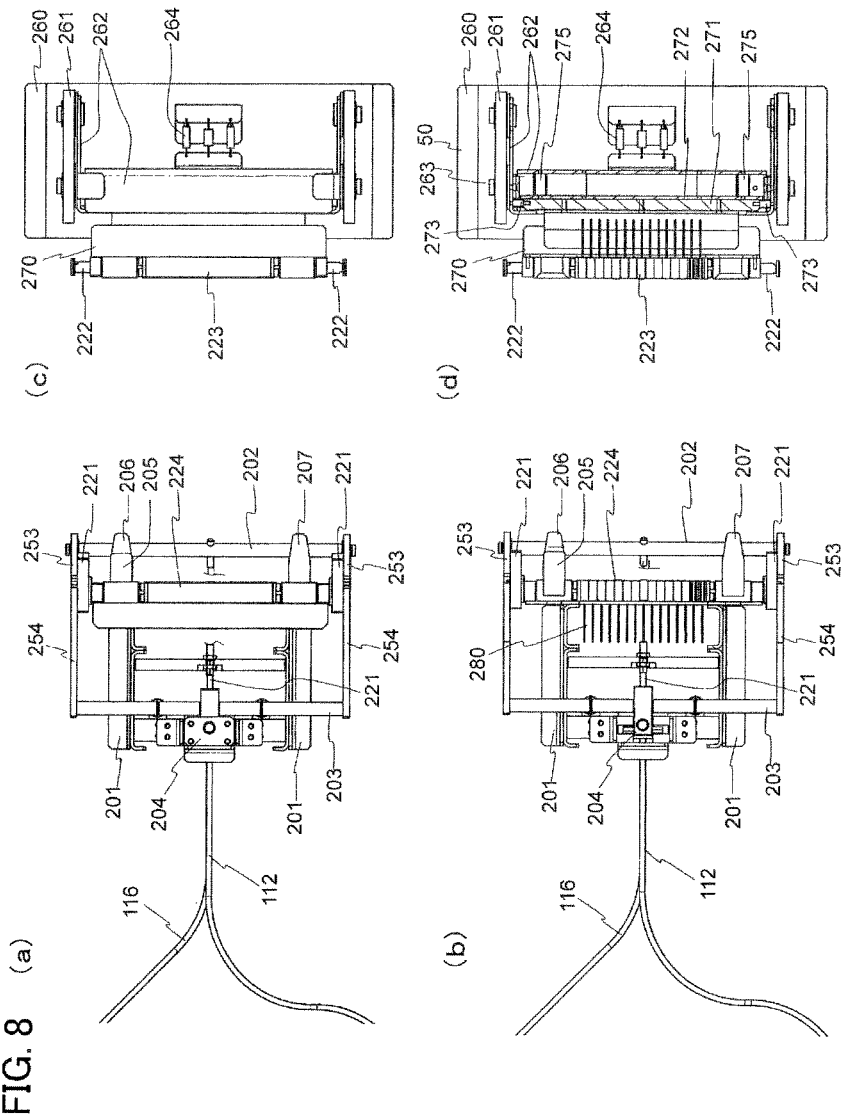
FIG. 8(a) is a top view of the docking unit 4 from which the cover is removed.
FIG. 8(b) is a cross-sectional view, taken along A-A of FIG. 4, of the docking unit 4 from which the cover is removed.
FIG. 8(c) is a top view of the docking unit 5 from which the cover is removed.
FIG. 8(d) is a cross-sectional view, taken along B-B FIG. 4, of the docking unit 5 from which the cover is removed.
Figure 9:
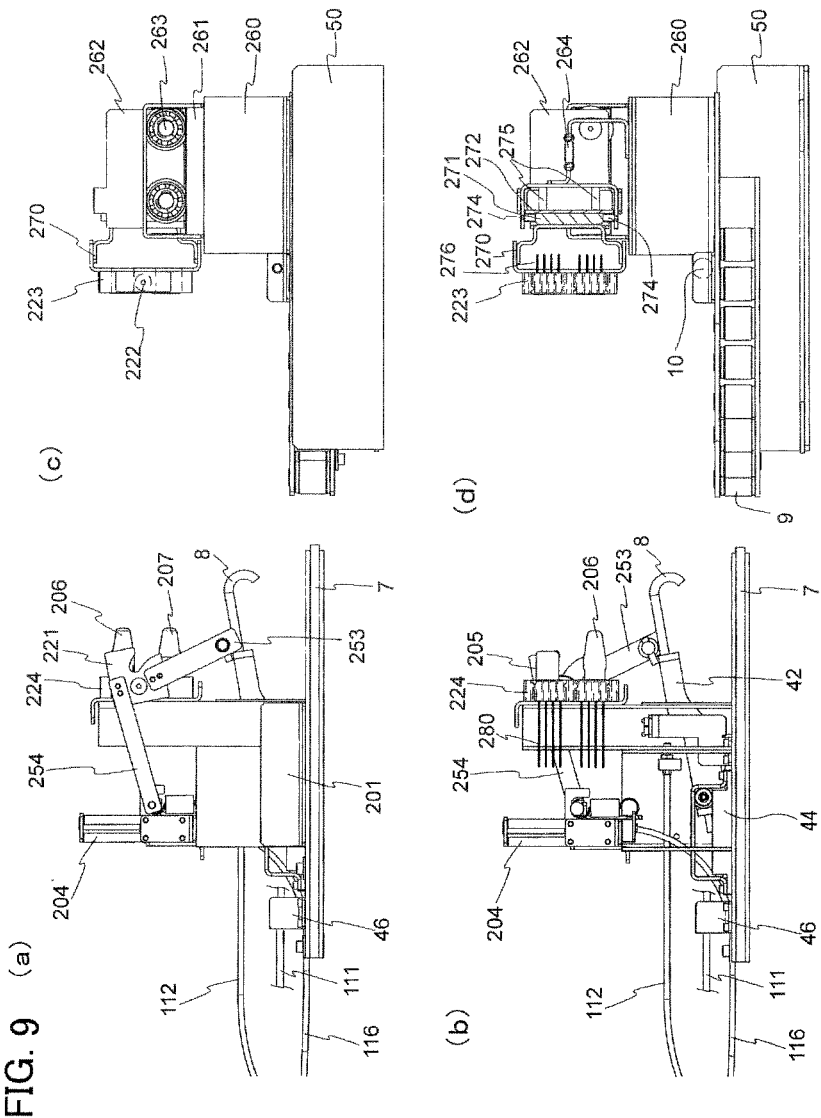
FIG. 9(a) is a side view of the docking unit 4 from which the cover is removed, FIG. 8 (b) is a cross-sectional view, taken along C-C of FIG. 5, of the docking unit 4 from which the cover is removed, FIG. 8 (c) is a side view of the docking unit 5 from which the cover is removed, and FIG. 8 (d) is a cross-sectional view, taken along D-D FIG. 5, of the docking unit 5 from which the cover is removed.

FIG. 3 is a perspective view of the bed 2 in a state where covers 37 and 53 are removed from the docking units 4 and 5 of FIG. 2, and is a perspective view of the docking unit 5 (the apparatus main body 2 is omitted). FIGS. 4 and 5 are perspective views of the docking units 4 and 5 from which the covers 37 and 53 are removed. FIG. 6 is a perspective view in a state where the cover 37, the electric connector 224, and its drive mechanism are detached from the docking unit 4. FIG. 7 is an E-E cross-sectional view of the bed 3 coupled to the docking unit 5 (the covers 37 and 53 are removed and only a coupling plate 7 and rollers 9 are shown). FIG. 8 (a) is a top view of the docking unit 4 from which the cover 37 is removed, FIG. 8(b) is an A-A cross-sectional view of the docking unit 4 from which the cover 37 is removed, FIG. 8(c) is a top view of the docking unit 5 from which the cover 53 is removed, and FIG. 8(d) is a B-B cross-sectional view of the docking unit 5 from which the cover 53 is removed. However, the coupling plate 7, the hook 8, and the roller unit 50 are omitted in FIG. 8. FIG. 9(a) is a side view of the docking unit 4 from which the cover 37 is removed, FIG. 9(b) is a C-C cross-sectional view of the docking unit 4 from which the cover 37 is removed, FIG. 9(c) is a side view of the docking unit 5 from which the cover 53 is removed, and FIG. 9(d) is a D-D cross-sectional view of the docking unit 5 from which the cover 53 is removed.

As shown in FIGS. 3 to 5, the docking unit 4 on the bed 3 side includes the coupling plate 7 having one end fixed to a frame 34 of the bed 3, the hook 8, a drive mechanism 41 of the hook 8 the electric connector 224 mounted on the coupling plate 7 and hook-shaped coupling tools 221. Meanwhile, the docking unit 5 on the apparatus main body 2 side includes the roller unit 50 in which a plurality of rollers 9 are arranged, a coupling bar 10 for coupling with the hook 8, and an electric connector 223 mounted on the roller unit 50. Members that constitute the docking units 4 and 5 are all nonmagnetic members.

The coupling plate 7 of the docking unit 4 of the bed 3 is inserted into the roller unit 50 of the docking unit 5 of the apparatus main body 2, and the bed 3 is fixed in a lateral direction (the width direction of the bed 3) as the coupling plate 7 is sandwiched from side surface directions between the plurality of rollers 9, as shown in FIG. 7. Additionally, provided is a structure in which the bed 3 is fixed in the long-axis direction thereof as the hook 8 is coupled to the coupling bar 10. At this time, the cover 37 and the cover 53 of the docking units 4 and 5 are configured so that one cover enters the other cover and there is no collision.

As shown in FIG. 5, the outer shape of the coupling plate 7 is substantially trapezoidal, and has straight portions 51 on both sides and a curved portion 52 at a tip. By forming both the sides in a linear shape (straight portions 51), the coupling plate 7 can be strongly sandwiched and held by the rollers 9 from both the sides.

The drive mechanism 41 of the hook 8 is fixed at a predetermined position on the coupling plate 7. The drive mechanism 41 of the hook 8 includes a hook supporting portion 42 that is fixed to a base of the hook 8, protrusions 43 that are respectively fixed to both the sides of the hook supporting portion 42, slide guides 44 that slidably guide the protrusions 43 along the axial direction of the bed 3, a wire A 111 that is fixed to a rear end of the hook supporting portion 42, a wire guide 46, and a bar 47 on which the hook supporting portion 42 rides and that lifts the tip of the hook 8. The other end of the wire A 111 is coupled to the pedal 105 at a rear end of the bed 3. Additionally, a spring 48 is arranged between the rear end of the hook supporting portion 42 and the wire guide 46 to bias the hook supporting portion 42 in a direction in which the hook supporting portion is advanced to the front. In addition, although FIG. 5 is a perspective view, the spring 48 is drawn in a simplified manner for convenience of illustration.

Frame portions 201 erected while straddling the hook 8 and its mechanism unit 41 are arranged on the coupling plate 7 as shown in FIG. 4 and FIG. 5, and the electric connector 224 in which several tens of or several hundreds of connector pins are vertically and horizontally arrayed is fixed onto the frame portions 201 with a coupling surface being substantially vertically turned to the apparatus main body 2. Wiring lines 280 are respectively connected to the connector pins.

As shown in FIGS. 4, 5, 8, and 9, the coupling tools 221 are attached to both side surfaces of the electric connector 224 so as to be rotatable around a rotary shaft 250. An arm 253 and an arm 254 are attached to each of the coupling tools 221. The arms 253 of the left and right coupling tools 221 are coupled together by an arm coupling bar 202. The arms 254 of the left and right coupling tools 221 are coupled together by an arm coupling bar 203. One end of a wire B 112 is connected to the center of the arm coupling bar 202. The other end of the wire B 112 is connected to the pedal 106. One end of a wire C 116 is connected to a middle portion of the arm coupling bar 203 via a slide guide 204. The other end of the wire C 116 is connected to the pedal 107. The slide guide 204 is a mechanism that guides the movement of the arm coupling bar 203 so that the arm connector bar descends vertically.

Additionally, three locating pins 205, 206, and 207 are arranged on both sides of the coupling surface of the electric connector 224 so as to protrude perpendicular to the coupling surface. The locating pins 206 and 207 that are diagonally arranged are longer than the locating pin 205, and are made thinner at the tips thereof. When the electric connector 224 is coupled to the electric connector 223 of the docking unit, the tips of the locating pins 206 and 207 are inserted into the holes 216 and 217 provided at corresponding positions of both the sides of a coupling surface of the electric connector 223, whereby the electric connector 223 is roughly positioned with respect to the electric connector 224. Moreover, the bases of the short and thick locating pin 205 and the locating pins 206 and 207 are inserted into the holes 215, 216, and 217, thereby positioning the electric connector 223 with respect to the electric connector 224 with high precision. The electric connector 224 is provided with a movable mechanism that allows this positioning.

Meanwhile, as shown in FIG. 4, the roller unit 50 includes an upper plate 62, a lower plate 63, and the plurality of rollers 9 that are arranged between the upper plate 62 and the lower plate 63 and are rotatably fixed. The coupling plate 7 of the bed 3 is inserted into a space between the upper plate 62 and the lower plate 63, and side surfaces thereof are held by supporting rollers 12 within the rollers 9. The remaining rollers are guide rollers 13 that guide the coupling plate 7. The coupling bar 10 is fixed to a predetermined position on the upper plate 62. The portion of the upper plate 62 closer to the near side than the coupling bar 10 is cut out. Accordingly, when the coupling plate 7 is inserted into the roller unit 50, the hook 8, its drive mechanism 41, and the electric connector 224 on the coupling plate 7 approach the coupling bar 10 without colliding against the upper plate 62, and are arranged at positions where coupling is allowed.

A frame portion 260 is arranged on the upper plate 62 of the roller unit 50 so as to straddle the coupling bar 10. Slide guides 261 are fixed onto the frame portion 260. Projections 263 on both the sides of the outer slide frame 262 are inserted into the slide guides 261, and thereby, the outer slide frame 262 is supported by the slide guides 261 so as to be slidable in the long-axis direction of the bed 3. As shown in FIG. 4, springs 264 are fixed to a rear surface of the outer slide frame 262, and bias the outer slide frame 262 with respect to the frame portion 260 so as to pull the outer slide frame in the long-axis direction of the bed 3 in a direction away from the bed 3. Accordingly, when the electric connector 223 is removed from the coupling tools 221 on the electric connector 224 side, the outer slide frame 262 functions to slide back so as to be away from the bed 3, and to separate the electric connector 223 from the electric connector 224.

A movable mechanism making the electric connector 223 movable in three axial directions is built inside the outer slide frame 262 for the positioning of the electric connector, and the electric connector 223 is supported via the movable mechanism. Sockets for coupling with the connector pins of the electric connector 224 are vertically and horizontally arranged on the coupling surface of the electric connector 224. The coupling surface of the electric connector 224 is arranged substantially vertically toward the bed 3. Both side surfaces of the electric connector 224 are equipped with projections (pins) 222 for coupling with the coupling tools 221. Additionally, both sides of the coupling surface are equipped with the above-described positioning holes 215, 216, and 217.

Figure 10:
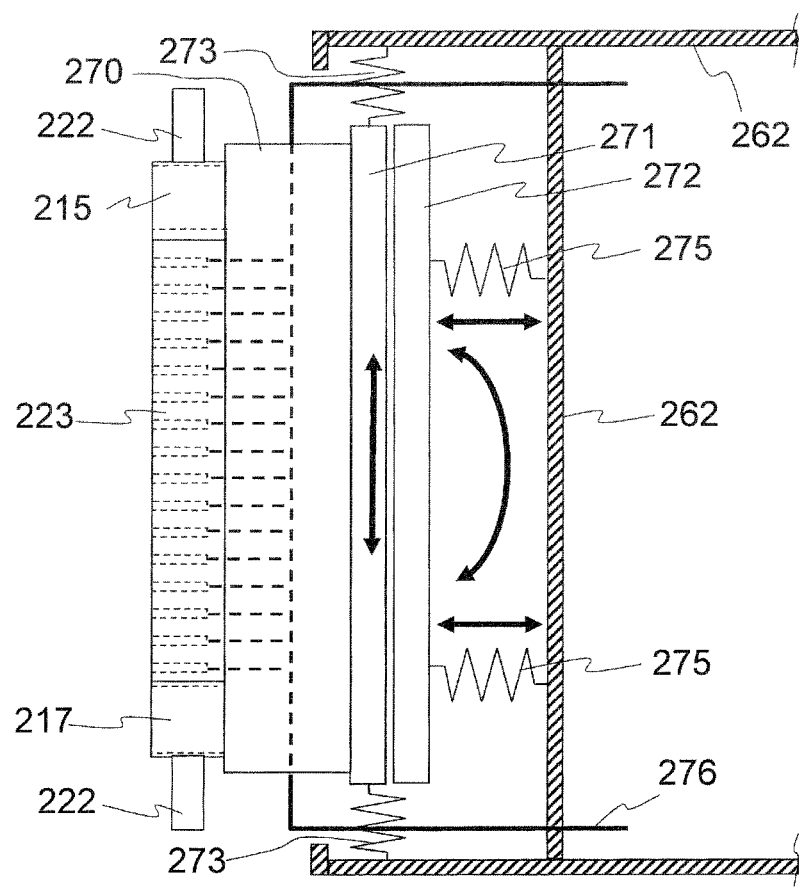
FIG. 10 is a simplified block diagram of FIG. 8(d).
Figure 11:
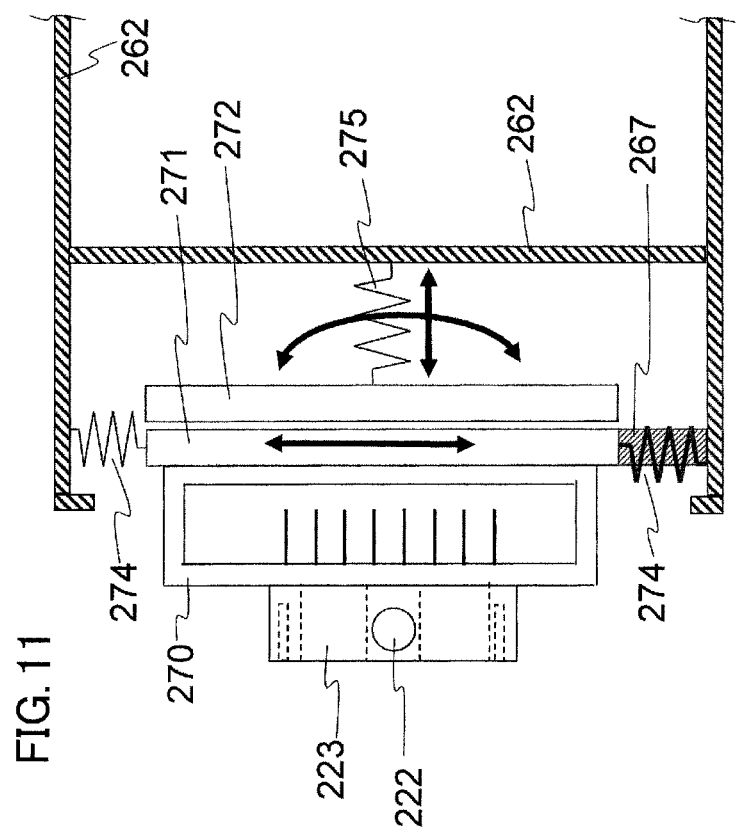
FIG. 11 is a simplified block diagram of FIG. 9(d).

The movable mechanism in the outer slide frame 262 will be further described with reference to FIGS. 8 to 11. FIG. 10 is a simplified block diagram of FIG. 8(d), and FIG. 11 is a simplified block diagram of FIG. 9(d).

As shown in FIGS. 8(d), 9(d), 10, and 11, a sliding plate 271 coupled to inner walls of the outer slide frame 262 with four springs 273 and 274 arranged on the left and right sides and upper and lower sides of the coupling surface of the electric connector 223, and a sliding plate 272 having a rear surface coupled to the outer slide frame 262 with left and right springs 275 are arranged in the outer slide frame 262 so as to be substantially vertically turned and overlapping each other. The electric connector 223 is fixed to a front surface of the sliding plate 271 via a connector supporting frame 270. The sliding plates 271 and 272 are made of a nonmagnetic substance, such as resin, having excellent slidability. An end portion of a wiring line 276 connected to the electric connector 223 is drawn around within the connector supporting frame 270.

Accordingly, the sliding plate 271 supported by the springs on the left and right sides and upper and lower sides slides with respect to the sliding plate 272 and is horizontally and vertically movable, and when the sliding plate 271 is pushed in the direction of a rear surface, the sliding plate 272 is withdrawn backward and supports the sliding plate 271. Accordingly, the sliding plate 271 can support the electric connector 223 so as to be displaceable vertically and horizontally, backward, horizontally obliquely, and vertically obliquely (supinely). Hence, when the locating pins 205 to 207 of the coupling connector 224 are inserted into the holes 215 to 217 of the coupling connector 223, the coupling connector can be displaced vertically and horizontally, backwardly, horizontally obliquely, and vertically obliquely (supinely) to align the coupling connector 223 with the coupling connector 224.

In addition, an elastic member 277 that assists the springs 274 sustaining the weight of the sliding plate 271 is arranged at a lower ion of the sliding plate 271.

Here, the operation of the respective portions when the bed 3 is docked with the apparatus main body 2 will be described. If an examiner holds the handle portion 11 of the bed 3 to move the bed toward the apparatus main body 2 and the bed 3 approaches the apparatus main body 2, the coupling plate 7 of the bed 3 contacts the guide rollers 13 among the rollers 9 of the roller unit 50 of the apparatus main body 2, the deviations of the position and an angle of the bed 3 with respect to the apparatus main body 2 are corrected, and the tip of the coupling plate 7 is inserted between the rollers 9. As shown in FIG. 7, if the coupling plate 7 is sandwiched by four supporting rollers 12 arranged at a position where the coupling plate 7 is sandwiched among the rollers 9, the coupling plate cannot be inserted any more; therefore, the movement of the bed 3 stops. This position is a docking position. In addition, in FIG. 7, only the rollers 9 of the docking unit 5 are shown and only the coupling plate 7 of the docking unit 4 is shown.

If the bed 3 is inserted into the docking position and the examiner steps on the pedal 105, the wire A 111 is pulled, and the hook 8 moves in a direction in which the hook is pulled to the rear side (bed 3 side) while descending, and is coupled to the coupling bar 10 on the apparatus main body 2 side. From the above, a mechanical docking operation is completed.

By the mechanical docking operation, the electric connector 224 on the coupling plate 7 approaches the electric connector 223 on the roller unit 50, as shown in FIG. 12(a).

As for the positional relationship between the electric connectors 223 and 224 in a state (docking position) where the mechanical docking is completed, as shown in FIG. 12(b), the electric connectors 224 and 223 face each other with a predetermined spacing t. The long locating pins 207 and 206 that are located diagonally on both the sides of the electric connector 224 are designed to be longer than the spacing t. For this reason, the tips of the locating pins 207 and 206 are inserted into the holes 217 and 216 of the electric connector 223, and displace the electric connector 223 vertically and horizontally, forwardly and backwardly, horizontally obliquely, and vertically obliquely to achieve rough alignment. The displacements in the vertical and horizontal directions, in the forward and rearward directions, the horizontally oblique direction, and in the vertically oblique direction are realized as the sliding plates 271 and 272 within the outer slide frame 262 are displaced. Additionally, since the short locating pin 205 is designed to be shorter than the spacing t, this pin is not inserted into the hole 215 yet. Additionally, the spacing t between the electric connectors 224 and 223 at this time is designed so as to fall within a range where the outer slide frame 262 is slidable.

Here, if the examiner steps on the pedal 106, the wire B 112 is pulled and the arms 253 turns, whereby the coupling tools 221 rotate around the shaft 250 as shown in FIG. 12(c). Accordingly, the pins 222 are pulled into recesses of the coupling tools 221, and the coupling tools 221 draw the electric connector 224 near. Accordingly, when the outer slide frame 262 moves to the near side along the slide guides 261, the electric connector 224 moves to the electric connector 223 side, and is coupled to the electric connector 224.

At this time, as the bases of the thick short locating pin 205 and the long locating pins 206 and 207 of the electric connector 223 are inserted respectively into the holes 215 to 217 of the electric connector 224, the electric connector 223 is displaced vertically and horizontally, forwardly and backwardly, horizontally obliquely, and vertically obliquely, and is aligned with the electric connector 224 with high precision. Hence, a number of connector pins can be precisely inserted into the sockets without being damaged.

From the above, with the mechanical docking, the electric connector 224 equipped with several tens of or several hundreds of pins and the electric connector 223 equipped with the sockets corresponding to these pins can be aligned with each other precisely and coupled to each other. Hence, the examiner does not need to manually couple the connectors, and electric connection can be easily and reliably performed together with the mechanical docking. Additionally, since the alignment is precisely performed, the connector pins are not damaged.

In contrast, when the bed 3 is separated from the apparatus main body 2, the examiner steps on the pedal 107 shallowly, and the wire C 116 pulls down the arms 254 and loosens the wire B 112, thereby rotating the coupling tools 221 in the opposite direction as shown in FIG. 12(d). Accordingly, the pins 222 are separated from the coupling tools 211, and the electric connector 223 can also be withdrawn backward with a force with which the springs 264 withdraw the outer slide frame 262 backward, and can be separated from the electric connector 224.

If the examiner further stepson the pedal 107 and loosens the wire A 111, the hook 8 is lifted and separated from the coupling bar 10. Accordingly, the electric connectors and the hook 8 are released in this order. If the examiner holds the handle portion 11 and pulls the bed backward, the bed 3 can be separated from the apparatus main body 2.

From the above, the docking units 4 and 5 that can perform electrical docking by the mechanism units after the mechanical docking can be provided.

In addition, the pedals 105 and 106 are equipped with pedal unit mechanisms that do not receive an operation if the operation is not an operation in order of the pedal 105 and the pedal 106. This configuration will be described in detail below.

<Second Embodiment>

Figure 13:
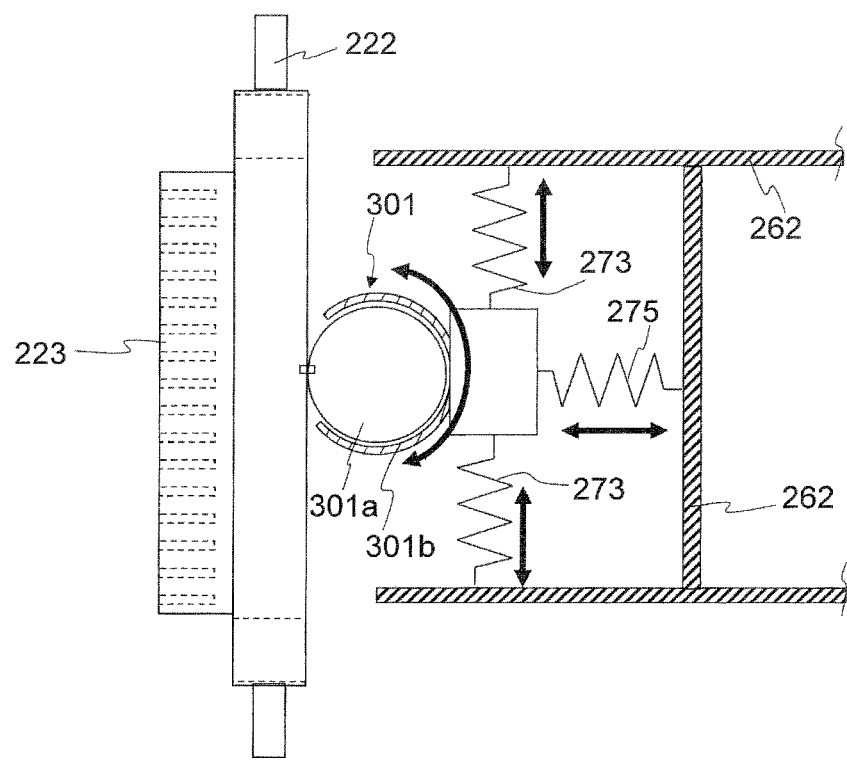
FIG. 13 is a block diagram showing a movable mechanism within an outer slide frame 262 of a second embodiment.

In the first embodiment, the sliding plates 271 and 272 are used to make the electric connector 223 movable horizontally, vertically, forwardly, and backwardly with respect to the outer slide frame 262, but the invention is not limited to this. In the second embodiment, as shown in FIG. 13, a ball joint 301 is used instead of the sliding plates 271 and 272. The ball joint includes a ball 301a and a supporting portion 301b that rotatably supports this ball, and fixes the ball 301a to the electric connector 223 or the connector supporting frame 270. The supporting portion 301b is supported by springs 273, 274, and 275.

By virtue of the configuration of FIG. 13, the electric connector 223 can be supported so as to be displaceable vertically and horizontally, horizonally obliquely, and vertically obliquely (supinely); therefore, the same functions as in the first embodiment is obtained.

Since the other configuration is the same as that of the first embodiment, the description thereof will be omitted.

<Third Embodiment>

Figure 14:
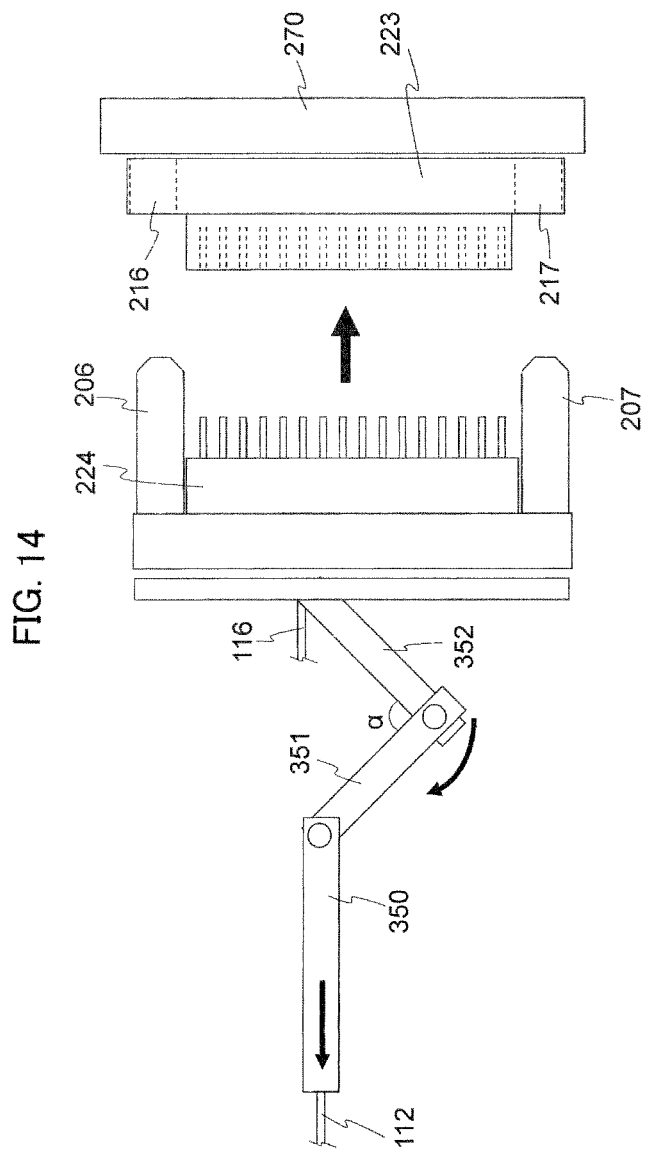
FIG. 14 is a block diagram showing a movable mechanism of an electric connector 224 of a third embodiment.

In the first embodiment, the electric connector 223 on the apparatus main body 2 side is configured to be slidable with respect to the outer slide frame 262 and the electric connector 224 side is fixed, but the invention is not limited to this configuration. The third embodiment has a configuration in which a link mechanism having a plurality of arms 351, 352, and 353 coupled to each other in order is arranged on a rear surface of the electric connector 224 as shown in FIG. 14, and the electric connector 229 is pushed out toward and coupled to the electric connector 223 through the operation of the link mechanism.

In this link mechanism, an end portion of the wire B 112 is connected to the end portion of the arm 350. If an examiner steps on the pedal 106 and pulls the wire B 112, the arm 350 pulls the arm 351, an angle θ formed between the arm 351 and the arm 352 is widened, and the electric connector 229 is pushed out toward the electric connector 223. Accordingly, the electric connector 224 can be pushed against and coupled to the electric connector 223.

Additionally, the end portion of the wire C 116 is connected to a coupling portion of the arm 352 and the electric connector 224. If the examiner steps on the pedal 107 and pulls the wire C 116, an angle θ formed between the arm 351 and the arm 352 is narrowed, and the electric connector 224 is separated from the electric connector 223.

In this way, in the configuration of the third embodiment, even if there is no sliding mechanism, such as the outer slide frame 262, in the electric connector 223, the electric connector 224 can be moved and coupled to or decoupled from the electric connector 223. Additionally, the coupling tools 221 are also unnecessary.

In addition, it is also possible to arrange the vertically, horizontally, forwardly, and backwardly movable mechanism within the outer slide frame 262 on the electric connector 223 side similarly to the first or the second embodiment, and it is also possible to arrange the movable mechanism on the electric connector 224 side. Accordingly, the electric connector 223 and the electric connector 224 can be aligned with each other by the locating pins 205 to 207.

Since the other configuration is the same as that of the first embodiment, the description thereof will be omitted.

Additionally, it is also possible to arrange the sliding mechanism of the outer slide frame 262 and the vertically, horizontally, forwardly, and backwardly movable mechanism within the outer slide frame 262 in the first embodiment on the electric connector 224 side.

<Configuration of Coupling Plate 7 and Roller Unit 50>

Here, the configuration of the coupling plate 7 and the roller unit 50 that are arranged within the docking units 4 and 5 of the above-described first to third embodiments will be described in more detail.

As shown in FIG. 6, the outer shape of the coupling plate 7 is substantially trapezoidal, and has the straight portions 51 on both sides and the curved portion 52 at a tip. In the invention, by forming both the sides in a linear shape (straight portions 51), the coupling plate 7 can be strongly sandwiched and held by the rollers 9 from both the sides. The coupling plate 7 has a shape such that rubber 73 is sandwiched between an upper plate 71 and a lower plate 72, both of which are substantially trapezoidal and made of a non-magnetic metal. The rubber 73 does not protrude further outward than the upper plate 71 and the lower plate 72 in the portions of the straight portions 51 on both the sides, and slightly protrudes outward from the upper plate 71 and the lower plate 72 only in the curved portion 52 at the tip. As the metallic upper plate 71 and lower plate 72 form the side surfaces of the coupling plate 7 at the straight portions in this way, the coupling plate 7 is held with a strong force by the rollers 9. Additionally, as the rubber 73 protrudes slightly in the curved portion 52 at the tip, the noise generated when the coupling plate 7 collides against the rollers 9 is reduced. The relationship between the outer shape of the coupling plate and a holding force will be further described below.

Figure 15:
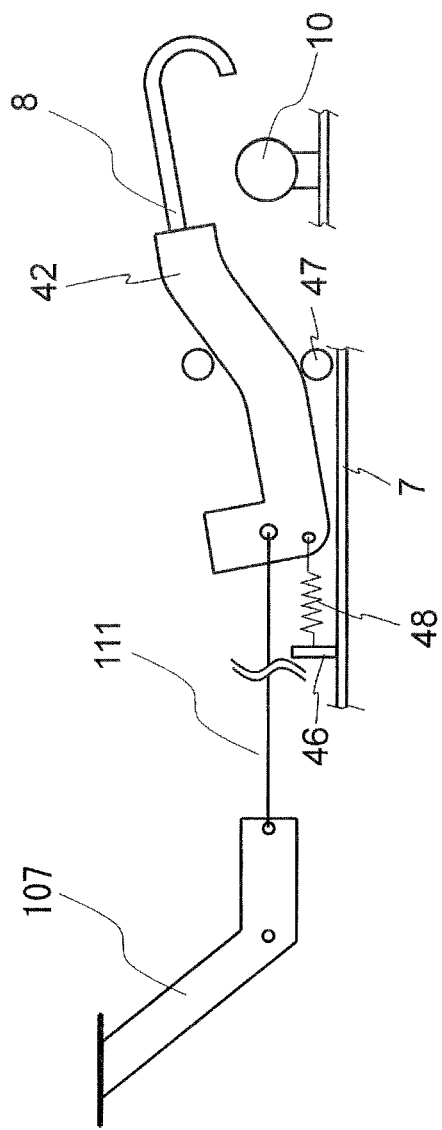
FIG. 15 is a view for explaining the operation of a hook 8 of the docking unit 4.

FIG. 15 shows the posture of the hook supporting portion 42, a pulling direction of the wire A 111, and a biasing direction of the spring 48. The hook supporting portion 42 is pushed out forward (in a direction of the hook 8) by the force of the spring 48 in a state where the wire A 111 is not pulled, that is, in the state of FIGS. 6 and 15, a lower surface of the hook supporting portion 42 rides on the bar 47, and the tip of the hook 8 is lifted. If the wire A 111 is pulled backward (in a direction of the pedal 6) through the operation of the pedal 6 by an examiner, the lower surface of the hook supporting portion 42 moves backward along the slide guides 44 while sliding on the upper surface of the bar 47. The lower surface of the hook supporting portion 42 is curved upward at a tip portion thereof. Therefore, as the tip curved upward as it moves backward comes to the position of the bar 47, the hook 8 at the tip moves backward while descending. Accordingly, the hook supporting portion is configured so as to be coupled to the coupling bar 10 on the apparatus main body 2 side. If the wire A 111 is loosened through the operation of the pedal 6, the spring 48 biases the hook supporting portion 42 in a direction in which the hook supporting portion is advanced to the front, the hook supporting portion 42 rides on the bar 47, and the hook 8 is lifted upward and separated from the coupling bar 10.

Figure 16:
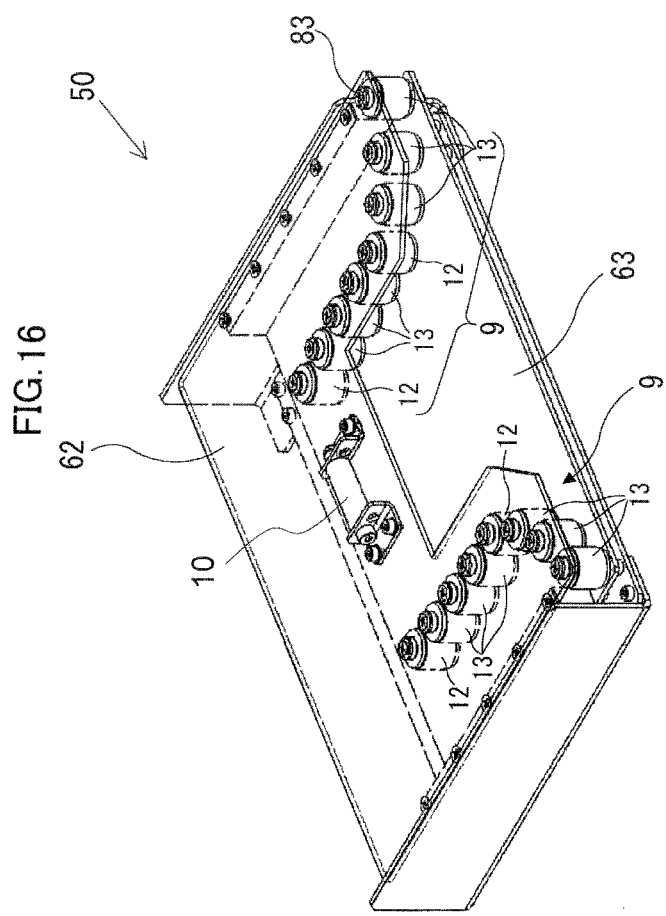
FIG. 16 is a perspective view of a roller unit 50 of the docking unit 5.

Meanwhile, the rollers 9 of the roller unit 50 are arrayed as shown in FIG. 16, and are constituted by the four supporting rollers 12 and the plurality of guide rollers 13. At a final docking position, the supporting rollers 12 contact the coupling plate 7 and sandwiches and fixes the coupling plate 7 from both the sides. When the coupling plate 7 is inserted into the roller unit 50, the guide rollers 13 function to guide the movement of the coupling plate 7 and lead the coupling plate to the docking position.

Figure 17:
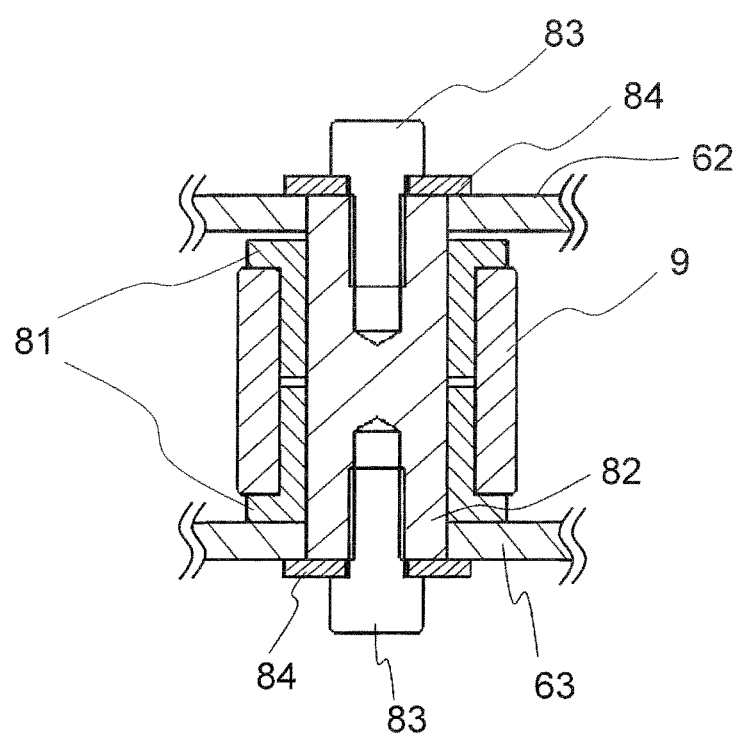
FIG. 17 is a cross-sectional view of a roller 9 of the roller unit 50.

A cross-sectional view of a roller 9 is shown in FIG. 17. A shaft 82 of the roller 9 has both ends firmly fixed to the upper plate 62 and the lower plate 63 by screws 83 and washers 84. A sliding bearing 81 is arranged at an outer periphery of the shaft 82, and the roller 9 is arranged at an outer periphery of the sliding bearing 81.

The roller 9 and the sliding bearing 81 are integrated and rotate around the shaft 82. The shaft 82 and the roller 9 are made of metal with high rigidity, and the sliding bearing 81 is also made of materials having high rigidity and excellent slidability. Accordingly, even if the coupling plate 7 is inserted into the roller unit 50 and advances while contacting the roller 9, the rollers 9 can sandwich and hold the inserted coupling plate 7 between the rollers 9 without being deformed and warped.

Figure 18:
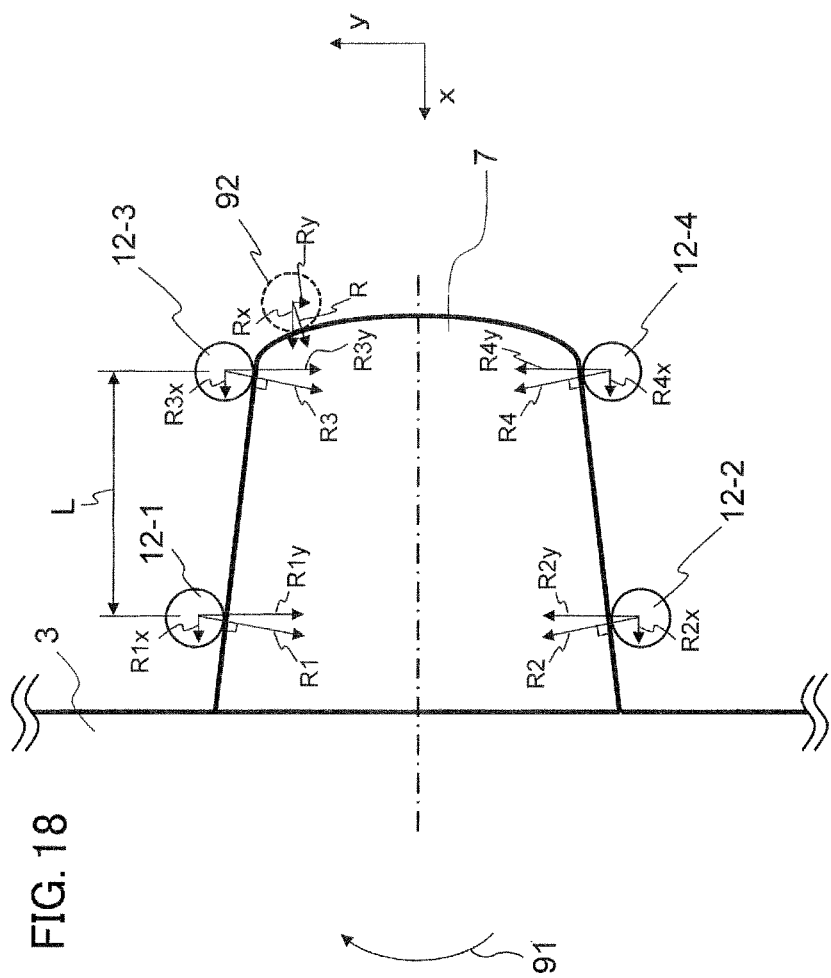
FIG. 18 is an explanatory view showing the positional relationship and roller reaction forces between supporting rollers 12 of the roller unit 50 and the coupling plate 7.

FIG. 18 is an explanatory view showing the positional relationship between the four supporting rollers 12 and the coupling plates 7 at the docking position. The four supporting rollers 12-1 to 12-4, as shown in FIG. 18, are arranged so as to sandwich the straight portions 51 of the coupling plate 7 from both the sides. Specifically, a pair of the supporting roller 12-1 and the supporting roller 12-2 are arranged face to face at the positions of the coupling plate 7 near the frame 34, and a pair of the supporting roller 12-3 and the supporting roller 12-4 are arranged face to face at positions near at the tip of the coupling plate 7. The spacing between the supporting rollers 12-1 and 12-2 and the spacing between the supporting rollers 12-3 and 12-4, as shown in FIGS. 7 and 18, are set to exactly the same widths as the widths of the positions of the coupling plate 7 at the docking position. That is, since the coupling plate 7 is substantially trapezoidal, the spacing between the supporting rollers 12-1 and 12-2 is wider than the spacing between the supporting rollers 12-3 and 12-4. Accordingly, the coupling plate 7 is sandwiched by the four supporting rollers 12 and does not advance forward any more, at the docking position of FIGS. 7 and 18, and is positioned by the four supporting roller 12 at the docking position.

Additionally, it is preferable that the spacing L between the supporting roller 12-1 or 12-2 and the supporting roller 12-3 or 12-4 be longer because the coupling plate 7 can be held with a large holding force even in a case where the bed 3 sways left and right or a force with which the bed turns around the coupling plate 7 works.

Figure 19:
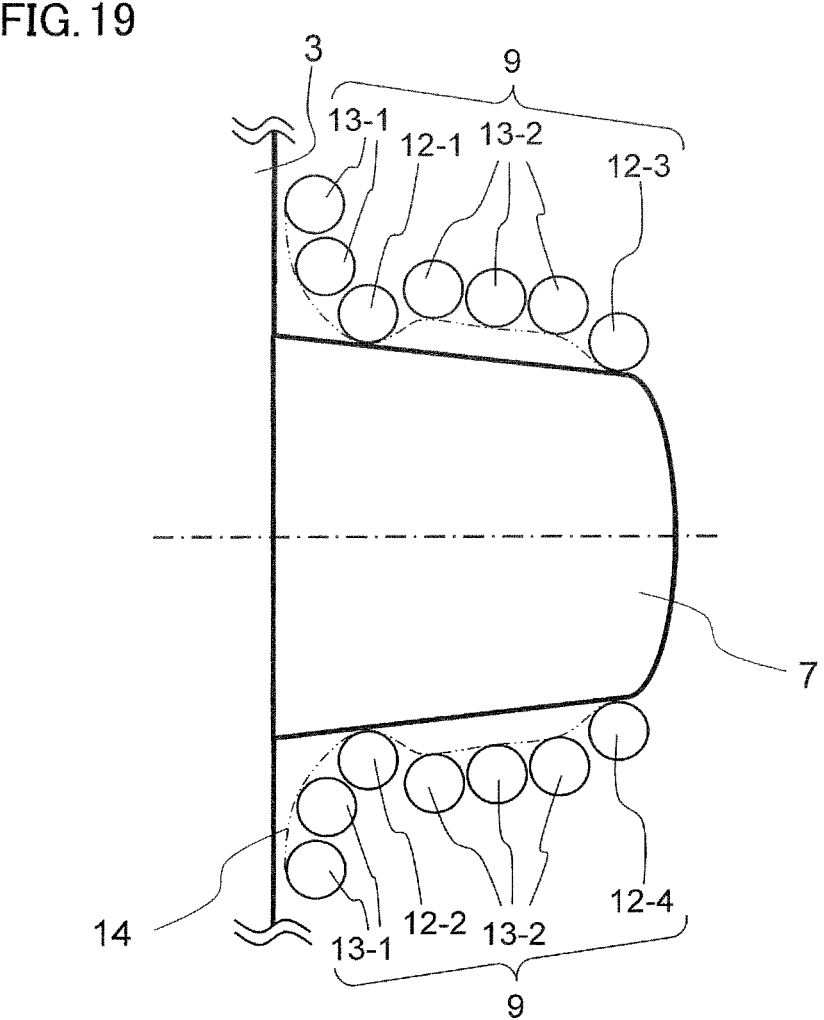
FIG. 19 is a top view showing the arrangement of the rollers 9 of the roller unit.

FIG. 19 is an explanatory view showing the positional relationship between the guide rollers 13 and the coupling plate 7 at the docking position. As shown in FIG. 19, the guide rollers 13-1 located further toward the bed 3 side than the supporting rollers 12-1 and 12-2 are arranged in a curved line 14 so as to constitute a frontage leading the coupling plate 7 between the supporting rollers 12-1 and 12-2, on an entrance side of the roller unit 50. That is, the spacing between the guide rollers 13-1 is wider than the spacing between the supporting roller 12-1 and the supporting roller 12-2 in a short-axis direction of the bed 3. Accordingly, the positional deviation of the bed 3 with respect to the apparatus main body 2 can be corrected, and the bed can be led to the docking position. The guide rollers 13-2 located between the supporting rollers 12-1 and 12-2 and the supporting rollers 12-3 and 12-4 are arranged so as to correct the orientation of the tips of the coupling plate 7 inserted into the supporting rollers 12-1 and 12-2 and lead the coupling plate between the supporting rollers 12-3 and 12-4. In addition, the guide rollers 13-1 and 13-2 are arranged so as to be offset to positions farther from the coupling plate 7 than the supporting rollers 12 so that, during docking, the four supporting rollers 12 reliably contact and hold the side surfaces of the coupling plate 7 and the guide rollers 13-1 and 13-2 do not contact the coupling plate 7.

Figure 20:
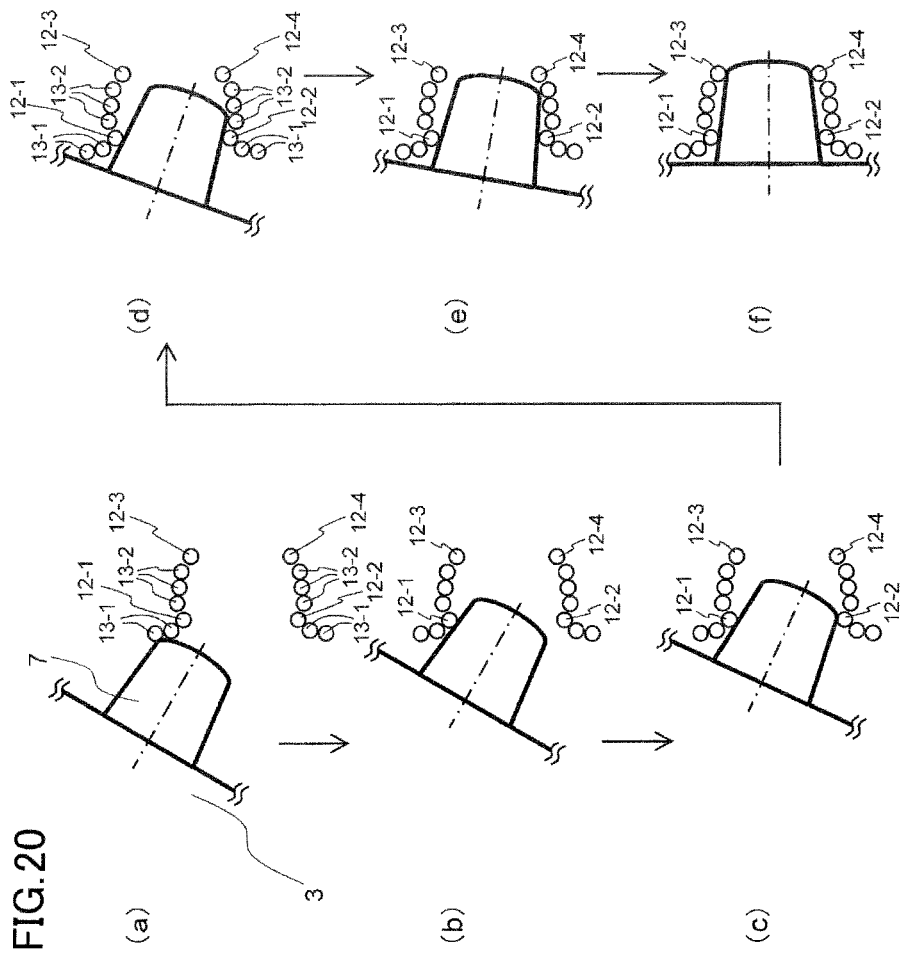
FIGS. 20(a) to 20(f) are views showing the operation of inserting the coupling plate 7 into the roller unit of FIG. 16.

The movement of the coupling plate 7 when the bed 3 is docked with the apparatus main body 2 will be described with reference to FIG. 20. An examiner holds the handle portion 11 of the bed 3 to move the bed toward the apparatus main body 2 during docking. Since the supporting rollers 12 and the guide rollers 13 are arranged at the roller unit 50 as described above, if the bed 3 approaches the apparatus main body, the coupling plate 7 of the bed 3 contacts the guide rollers 13-1 of the roller unit 50 of the apparatus main body 2, and the deviations of the position and the angle of the bed 3 with respect to the apparatus main body 2 are corrected (FIGS. 20($a$) and 20($b$)). Accordingly, the tip of the coupling plate 7 is inserted between the supporting rollers 12-1 and 12-2 (FIG. 20($c$)). If the examiner further advances the bed 3, the tip of the coupling plate 7 contacts the guide rollers 13-2, and thereby, the deviation of the position and the angle is corrected (FIGS. 20($d$) and 20($e$)), and the coupling plate is led between the supporting rollers 12-3 and 12-4 on the tip end side (FIG. 20($f$)). Since the coupling plate 7 cannot be inserted anymore if the coupling plate 7 is inserted to a position where the spacing between the supporting rollers 12-1 and 12-2, and the spacing between the supporting rollers 12-3 and 12-4 coincide with the widths of the coupling plate 7 at the positions of the supporting rollers, the movement of the bed 3 stops. This position is the docking position shown in FIG. 7.

As shown in FIG. 7, it can be seen that the bed 3 is held at the roller unit 50 of the apparatus main body 2 by the coupling plate 7 narrower than cane bellows portion 35 in the short-axis direction of the bed 3.

If the bed 3 is inserted into the docking position and the examiner operates the pedal 107 to pull the wire A 111, the hook 8 moves in the direction in which the hook is pulled to the rear side (bed 3 side) while descending, and is coupled to the coupling bar 10 on the apparatus main body 2 side. From the above, the docking operation is completed.

Here, the relationship between the shape of the coupling plate 7 and the holding force received from the supporting rollers 12 will be described with reference to FIG. 18. If an external force in the horizontal direction is applied to the bed 3 in a docking state, since the coupling plate 7 is pushed against the supporting rollers 12 by the external force, the coupling plate 7 receives roller reaction forces from the pushed supporting rollers 12. Roller reaction forces R1 to R4 are forces directed in directions perpendicular to the side surfaces of the coupling plate 7 from the respective supporting rollers 12-1 to 12-4. Component forces R1$y$ to R4$y$ in the horizontal direction y (the width direction of the bed 3) of the roller reaction forces and the external force are balanced with each other and hold the bed 3. For example, if the force of turning the bed 3 in a direction of arrow 91 of FIG. 18 is applied, the coupling plate 7 receives the roller reaction forces R1 and R4 from the supporting roller 12-1 and the supporting roller 12-4, and component forces R1$y$ and R4$y$ thereof in the horizontal direction are balanced with the external force, and the coupling plate 7 is held. That is, the force of turning the bed 3 can be cancelled by the moment of the supporting rollers 12 arranged in the long-axis direction of the bed 3.

Additionally, since the straight portions 51 incline, component forces R1$x$ to R4$x$ in a bed long-axis direction x of the roller reaction forces R1 to R4 are generated. The component forces R1$x$ to R4$x$ are forces in a direction in which the coupling plate 4 is pushed out from the apparatus main body 2. In the configuration of the present embodiment, the tension of the wire A 111 of the hook 8 is balanced with the component forces R1x to R4x, and thereby pushing-out of the coupling plate 4 is suppressed. The tension of the wire A 111 is designed to be greater than the total of R1x to R4x.

Here, if the supporting rollers 12 contact the curved portion 52 of the coupling plate 7 as in a roller 92 shown by a dotted line in FIG. 18, the component forces by in the horizontal direction of the roller reaction forces R become small, and the component forces Rx in the bed long-axis direction become large. For this reason, the force of holding the bed 3 in the horizontal direction becomes small, whereas the force of pushing out the bed 3 from the apparatus main body 2 becomes large. Therefore, in the present embodiment, it is desirable to arrange the four rollers 9 so as to contact the straight portions of the coupling plate 7.

Additionally, in the present embodiment, the coupling plate 7 is made substantially trapezoidal and the straight portions 51 are inclined. Therefore, when the bed 3 is attached to and detached from the apparatus main body 2, as shown in FIG. 20, the bed can be inserted into the docking unit 5 of the apparatus main body 2 from an oblique direction or can be separated from the docking unit in an oblique direction.

Accordingly, even if an electromagnetic shielding chamber in which the apparatus main body 2 is arranged is narrow, it is possible to attach and detach the bed 3.

However, the invention is not limited to the substantially trapezoidal coupling plate 7. When the electromagnetic shielding chamber in which the apparatus main body 2 is arranged is sufficiently wide and the bed 3 can be straightly lowered until the coupling plate 7 is separated from the roller unit 50, it is also possible to form the coupling plate 7 into a substantially oblong shape. In this case, since the component forces R1x to R4x in the bed long-axis direction x of the roller reaction forces R1 to R4 are not generated, all the roller reaction forces can be used so as to be balanced with the external force in the horizontal direction applied to the bed 3, and the holding force can be improved. Additionally, it is possible to make the tension of the wire A 111 small.

Additionally, in the present embodiment, the guide rollers 13 are arranged. However, it is also possible to omit some or all of the plurality of guide rollers 13.

As described above, the configuration of the present embodiment is a configuration in which the external force applied in the horizontal direction of the bed 3 is received by the reaction forces of the two pairs of supporting rollers 12 arranged in the long-axis direction of the bed 3. Therefore, although it is preferable that the length (the long-axis direction of the bed 3) of the coupling plate 7 be longer, it is not necessary to increase the width of the coupling plate 7. For this reason, although the configuration of the present embodiment is a configuration in which the bed 3 and the apparatus main body 2 can be coupled by a sufficient holding force during docking, the bed can be sufficiently held even if the width (the short-axis direction of the bed 3) of the coupling plate 7 is narrow. In the example of FIG. 7, the width (the short-axis direction of the bed 3) of the coupling plate is narrower than the width (the short-axis direction of the bed 3) of the bellows portion 35. In this way, a narrow docking mechanism that does not hinder the examiner's access to an object can be provided.

In the present embodiment, the coupling plate 7 is arranged on the bed 3 side and the roller unit 50 is arranged on the apparatus main body 2 side. However, it is also possible to arrange the roller unit 50 on the bed 3 side and to arrange the coupling plate 7 on the apparatus main body 2 side. It should be noted that it is more preferable to arrange the coupling plate 7 on the bed 3 side in the viewpoint of ensuring a wider space under the examiner's feet at a lower portion of the bed 3 because the width of the roller unit 50 becomes greater than the width of the coupling plate 7 structurally.

Additionally, by installing the guide rollers 13 in addition to the supporting rollers 12, the allowable width of the positional deviation of the bed 3 with respect to the apparatus main body 2 is large, and the examiner's work of docking the bed 3 with the apparatus main body 2 can be easily performed.

Additionally, by arranging the guide rollers 13 in a curved line, the coupling plate 7 can be smoothly inserted into the roller unit 50.

Additionally, the present embodiment is configured so that the rubber 73 is sandwiched between the upper plate 71 and the lower plate 72 of the coupling plate 7 and the rubber 73 protrudes only in the curved portion 52. However, it is also possible to form the side surfaces of the coupling plate 7 only from a metal plate without arranging the rubber 73.

A roller unit 50 of another embodiment will be described with reference to FIG. 21. In the roller unit 50 shown in FIG. 21, supporting pins 1120 and guide pins 1130 that are not rollers (do not rotate) are used instead of the supporting rollers 12 and the guide rollers 13 of the first embodiment. The positions of the supporting pins 1120 and the guide pins 1130 are the same as the positions of the supporting rollers 12 and the guide rollers 13, respectively. The other structure is made to be the some as that of the roller unit 50 of FIG. 16. Accordingly, the roller unit 50 of FIG. 21 can obtain almost the same functions as the roller unit 50 of FIG. 16.

Figure 21:
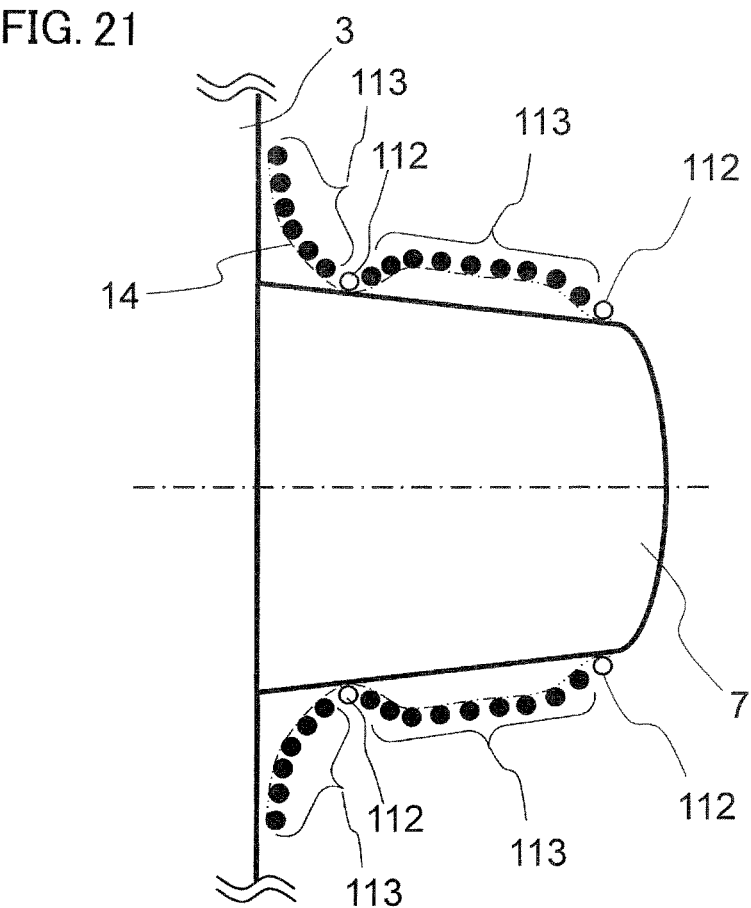
FIG. 21 is a view showing a coupling plate 7 of another embodiment and the positions of supporting pins 1120 and guide pins 1130 holding the coupling plate.

In the roller unit 50 of FIG. 21, the number of parts can be reduced because the shafts and bearings of the supporting rollers 12 and guide rollers 13 become unnecessary by using the supporting pins 1120 and guide pins 113 instead of the supporting rollers 12 and guide rollers 13.

Figure 22:
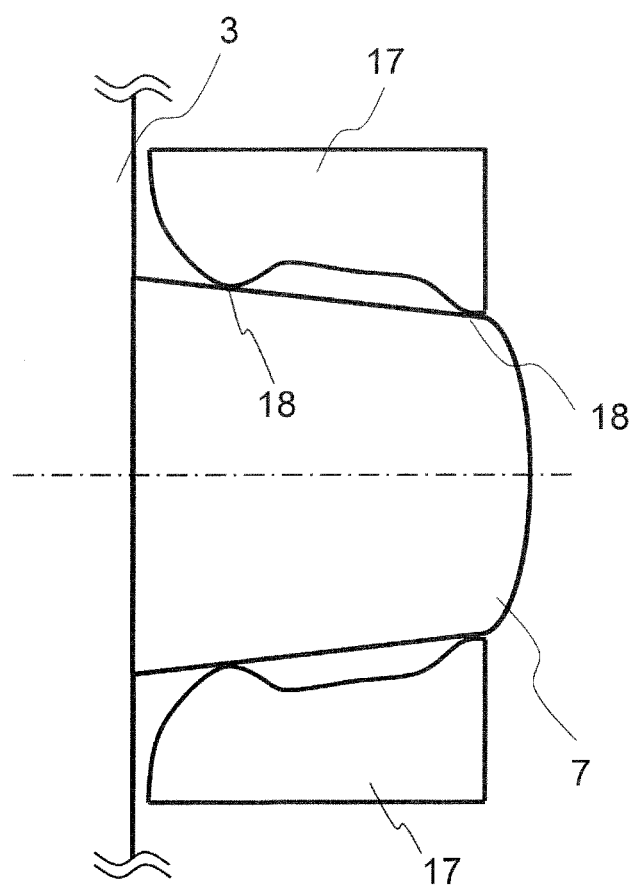
FIG. 22 is a view showing a coupling plate 7 of still another embodiment, and the shape of a guide wall 17 holding the coupling plate.

A roller unit 50 of still another embodiment will be described with reference to FIG. 22. A guide wall 17 in the same shape as the curved line 14 of FIG. 19 is installed instead of the supporting rollers 12 and the guide rollers 13 of the roller unit 50 of FIGS. 15 and 19. The guide wall 17 has supporting points 18 at the same positions as the four supporting rollers 12 of FIG. 16. During docking, the guide wall 17 contacts the coupling plate 7 at the four supporting points 18 and holds the coupling plate 7. The other portions of the guide wall 17 guide the insertion of the coupling plate 7, similar to the guide rollers 13 of FIG. 16. The other structure is made to be the same as that of the roller unit 50 of FIG. 16.

Accordingly, almost all of the same functions as the roller unit 50 can be obtained. Additionally, the number of parts can be reduced because the shafts and bearings of the rollers 12 and guide rollers 13 become unnecessary by using the guide wall 17 instead of the supporting rollers 12 and guide rollers 13.

It is desirable to select the material of the guide wail 17 so that friction does not become excessively large during contact with the material of the coupling plate 7. For example, one or both of the guide wall 17 and the coupling plate 7 are made of materials having excellent slidability.

Figure 23:
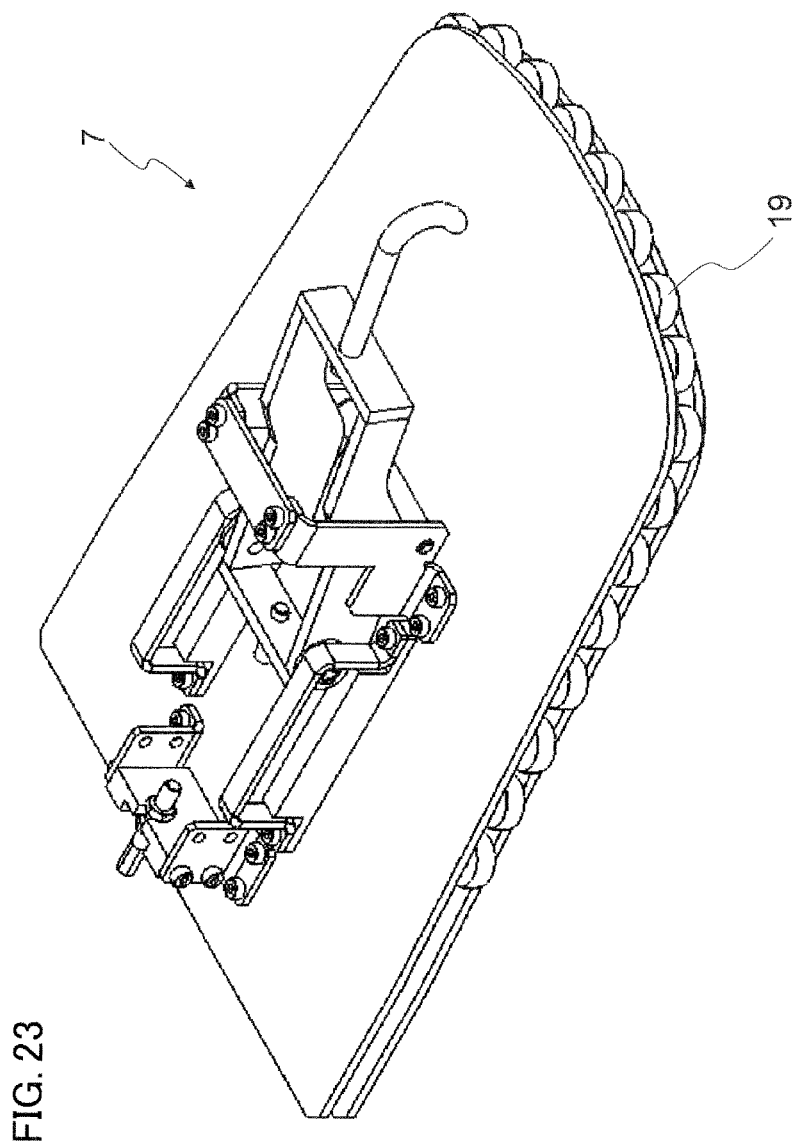
FIG. 23 is a perspective view of the coupling plate 7 including rollers at an outer periphery of the separate embodiment.

Additionally, as shown in FIG. 23, the coefficient of friction with the guide wall 17 can also be made low by installing coupling plate rollers 19 at an outer periphery of the coupling plate 7.

<Configuration of Pedal Unit>

The configuration of a pedal unit equipped with the pedals 105 to 107 arranged within the bed 3 of the above-described first to third embodiments will be described in more detail.

The three pedals 105, 106, and 107 are installed at the rear side end portion of the bed 3 as described above. When an attempt to couple the electric connectors are made in a state where the connector on the bed side and the connector on the apparatus main body side have positionally deviated, there is a risk that the connectors may collide with each other and damage the connector pins, in a state where the connectors have positionally deviated. In order to prevent this positional deviation, it is necessary to adopt en operating procedure in which, first, the bed and the apparatus main body are positioned and mechanically docked with each other, and the pedal 105 is operated and fixed by the hook, and thereafter, the pedal 106 is operated to electrically connect the electric connectors 223 and 224. Therefore, in the present embodiment, when the operating procedure of the pedals is erroneous, a pedal unit that allows an operator to notice an error without the pedal unit receiving an operation is mounted on the bed 3.

The pedal unit 104 does not receive an operation if the operation is not in the order of the pedal 105 and the pedal 106. Moreover, decoupling of the electric connectors and releasing of the hook for the mechanical docking may be performed in this order through the operation of the pedal 107.

Figure 24:
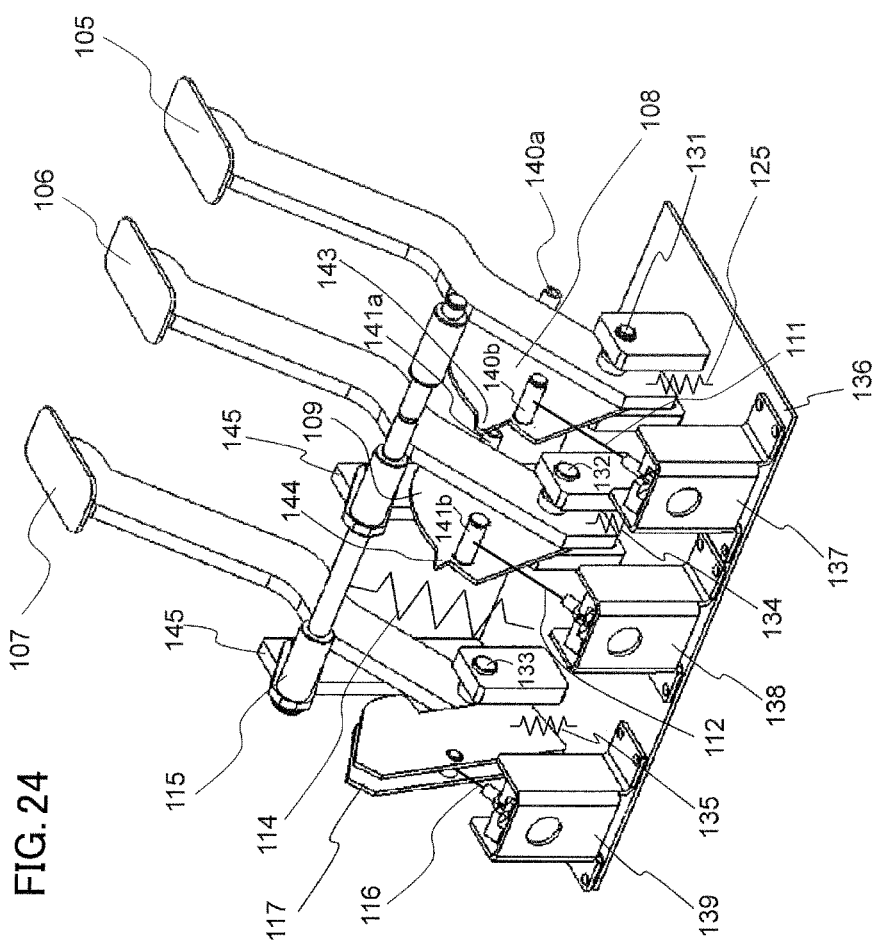
FIG. 24 is a perspective view of a pedal unit of the embodiments.

FIG. 24 is a perspective view of the pedal unit 104. It should be noted that the shape of springs 114, 125, and 132 or the like is drawn in a simplified manner in FIG. 24.

The pedal unit 104, as shown in FIG. 24, includes the three types of pedals 105 to 107, a substantially fan-shaped locking plate A (first plate) 108, a substantially fan-shaped locking plate B (second plate) 109, a release plate 117, a locking bar 115, wires A 111, B 112 and C 116, wire guides 137 to 139, and a supporting plate 136 that mounts these. The supporting plate 136 is fixed to the frame of the bed 3.

The pedals 105 to 107 have upper ends exposed to the outside of the cover 36 of the bed 3, and turn with shafts 131 to 133 as respective supporting points, as an operator steps on the upper ends with his/her foot. The shafts 131 to 133 are arranged so that central axes thereof coincide with each other. The locking plate A 108 and the locking plate B 109 are rotatably attached to the shafts 131 and 132 of the pedals 105 and 106, respectively. In the locking plate A 108 and the locking plate B 109, pedal-receiving shafts 140a and 141a are arranged at end portions in a circumferential direction, and shafts 140b and 141b for wire connection are arranged at end portions in the circumferential direction. When the pedals 105 and 106 are stepped on and turned, the pedals 105 and 106 push the pedal-receiving shafts 140a and 141b of the locking plate A 108 and the locking plate B 109, respectively; therefore, the locking plate A 108 and the locking plate B 109 are also configured to rotate. End portions of the wires A 111 and wire B 112 are fixed to the shafts 140b and 141b, respectively, for wire connection.

The release plate 117 is fixed to toe shaft 133 of the pedal 107, and rotates in conjunction with the turning of the pedal 107. An end portion of the wire 116 is fixed to the release plate 117.

Ends of springs 125 and 134 on one side are fixed to the pedals 105 and 106, respectively, and the other ends of the springs 125 and 134 are fixed to the supporting plate 136. The springs 125 and 134 are biased in a direction in which the springs returns to initial positions (positions of FIG. 24) thereof from a case where the pedals 105 and 106 are stepped on and turned by an examiner. Additionally, the pedal 107 and the release plate 117 that are coaxially fixed are biased in a direction in which the pedal and the release plate return to initial positions (positions of FIG. 24) thereof by a spring 135 attached to the release plate 117.

Figure 25:
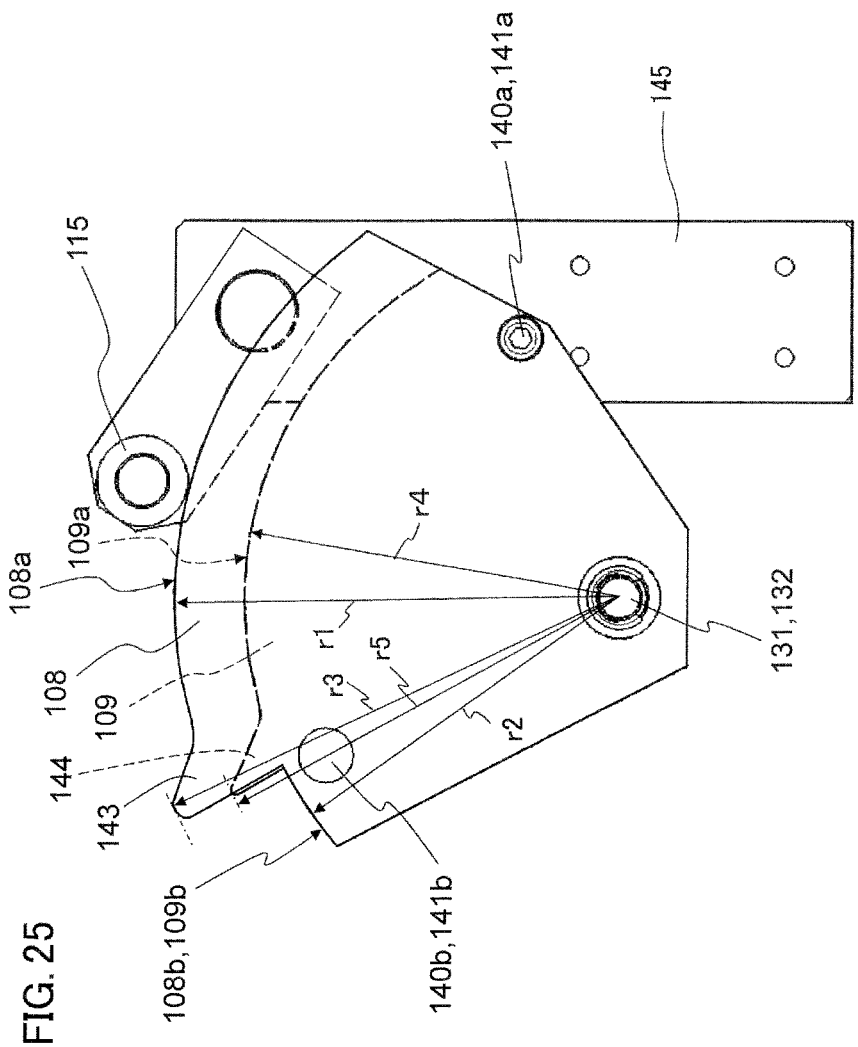
FIG. 25 is a side view of locking plate A 108 and locking plate 109 of the pedal unit of FIG. 24.

The substantially fan-shaped locking plate A 108 and locking plate B 109 include protrusions 143 and 144 at the same positions of outer peripheries thereof near the shafts 140b and 141b for wire connection, as shown in a side view of FIG. 25. In the locking plate A 108, the radius r1 of a circular-arc region 108a closer to the pedal-receiving shaft 140a side than the protrusion 143 is greater than the radius r2 of a cutout region 108b closer to the shaft 140b side for wire connection than the protrusion 143. The radius r3 of the highest position of the protrusion 143 is greater than the radius r1. In addition, the present embodiment, an outer periphery of the cutout region 108b is also formed in the shape of a circular arc. However, the cuter periphery may be linear without being limited to the circular-arc shape.

Meanwhile, in the locking plate B 109, the radius of a circular-arc region 109a closer to the side of the shaft 141b for wire connection than the protrusion 144 coincides with the radius r2 of a locking region 109b closer to the side of the shaft 140b for wire connection than the protrusion 143 of the locking plate A 108. The radius r4 of the locking plate B 109 on the pedal-receiving shaft 141a side is the same as the radius r2 of this locking plate closer to the shaft 141b for wire connection than the protrusion 144. The radius r5 of the highest position of the protrusion 144 is smaller than the radius r1. In addition, in the present embodiment, an outer periphery of the locking region 109b is also formed in the shape of a circular arc. However, the outer periphery may be linear without being limited to the circular-arc shape.

That is, in FIG. 25, the respective radii are designed so as to satisfy a relationship of r3>r1>r5>r4=r2.

Additionally, the side surfaces of the protrusions 143 and 144 on the pedal-receiving shaft 141a side incline with respect to the radial direction, and the side surfaces of the protrusions on the opposite side have a steeply rising shape that coincides with the radial direction.

The release plate 117 has a tip shape that inclines in order to push up the locking bar 115 against the force of the spring 114.

The locking bar 115 is arranged so as to stretch over the release plate 117, the locking plate A 108 and the locking plate B 109, and is supported by supporting portion 145. Tips of the supporting portions 145 are equipped with moving parts that make the supporting position of the locking bar 115 movable. Additionally, a spring 114 is attached to the locking bar 115, and is biased so as to be pushed against the outer peripheries of the locking plate A 108 and the locking plate B 109 or the tip of the release plate 117. In an initial state (FIG. 24), the locking bar 115 is in contact with the circular-arc region 108a (radius r1) of the locking plate A 108 with the largest radius, and is therefore not in contact with the locking plate B 109. The locking bar 115 includes rollers in the portions that contact the outer peripheries of the locking plate A 108 and the locking plate B 109 or the tip of the release plate 117, respectively.

Figure 12:
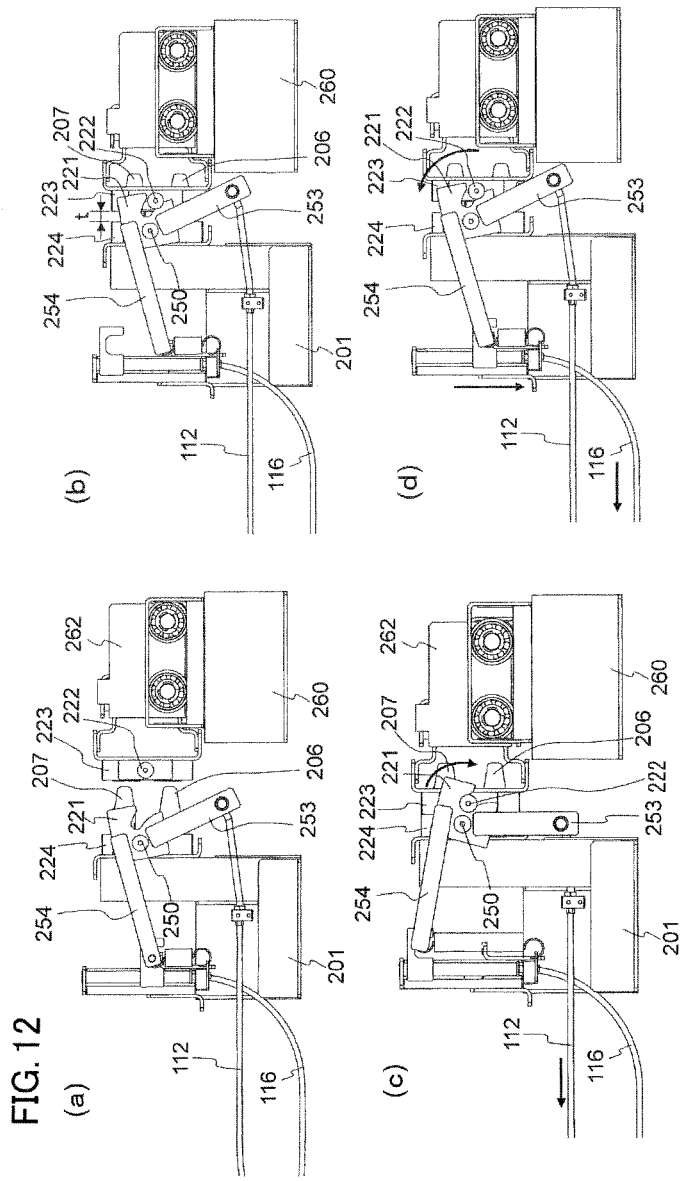
FIGS. 12(a) to 12(d) are side views showing a coupling operation of electric connectors 223 and 224 of FIG. 1.

As shown in FIG. 6, the hook 8 arranged within the docking unit 4 of the bed 3 is connected to the tip of the wire A 111 via the hock supporting portion 42. Meanwhile, as shown in FIG. 12 or the like, the tips of the wire B 112 and wire C 116 are connected to the coupling tools 221 of the electric connector 224 arranged within the docking unit 4 of the bed 3 via the arms 253 and 254 or the like.

The coupling tools 221 are pulled by the wire B 112 and are rotated around the rotary shaft 250 to couple the electric connectors 223 and 224. In contrast, as the wire C 116 is pulled and the coupling tools 221 are rotated in the opposite direction, the coupling is released.

Figure 26:
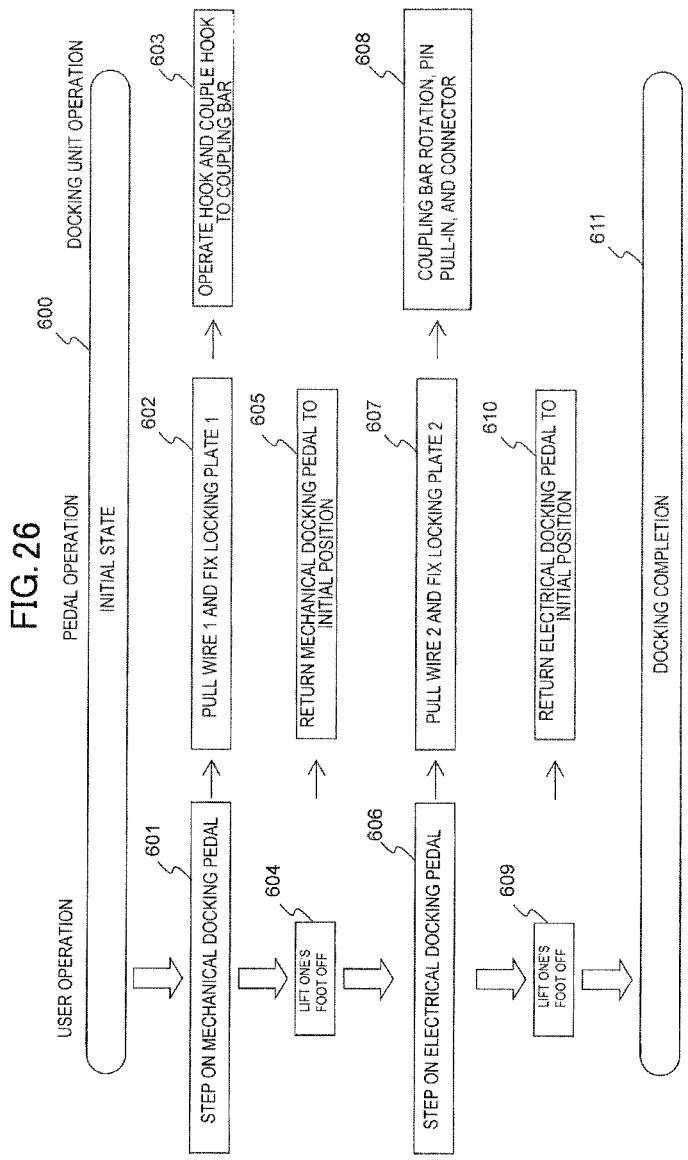
FIG. 26 is a block diagram showing the flow of operation for mechanically and electrically connecting the bed 3 of the embodiments to the apparatus main body.
Figure 27:
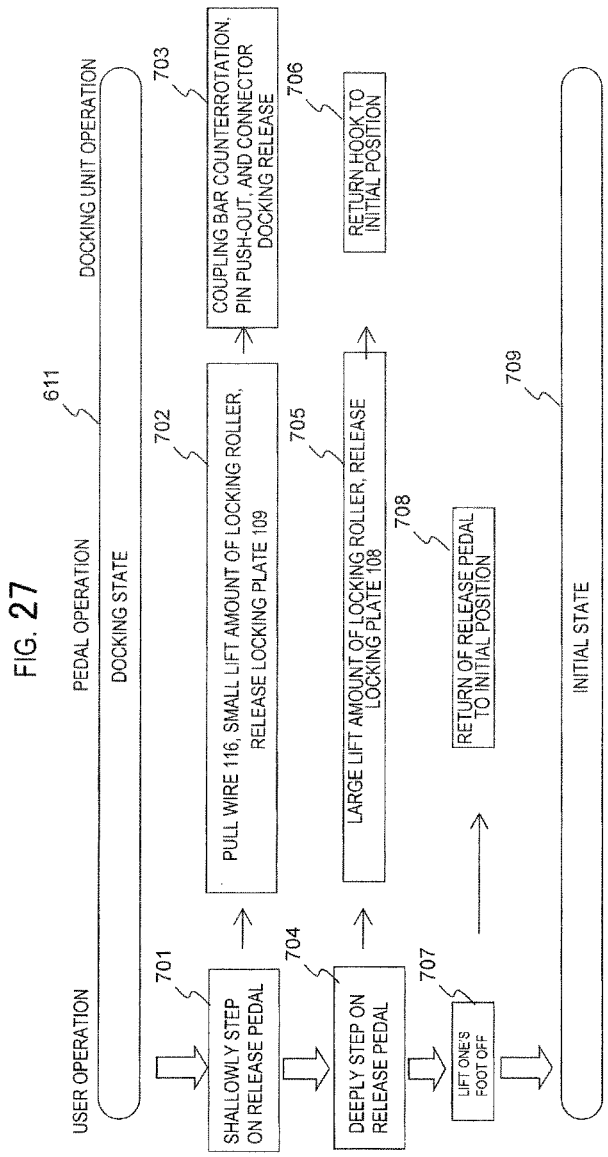
FIG. 27 is a block diagram showing the flow of operation for mechanically and electrically disconnecting the bed 3 of the embodiments from the apparatus main body.

The operation of the pedal unit 104 during the docking and separation of the bed 3 to/from the apparatus main body 2 will be described with reference to FIGS. 26 and 27. FIG. 26 is a block diagram showing the flow of the pedal operation during docking, and FIG. 27 is a block diagram showing the flow of the pedal operation during separation. In FIGS. 26 and 27, an operation performed by an operator is shown in a left column, the operation of a pedal is shown in a middle column, and the operation of the hook connector is shown in a right column.

During docking, an examiner holds the handle portion 11 of the bed 3 to move the bed toward the apparatus main body 2 and as described above, the coupling plate 7 of the docking unit 4 is inserted into the roller unit 50 within the docking unit 5. Accordingly, the bed 3 stops at the position where the bed 3 is coupled to the apparatus main body 2 as shown in FIG. 1. In this state, the pedal unit 104 is in the initial state of FIG. 24.

Figure 28:
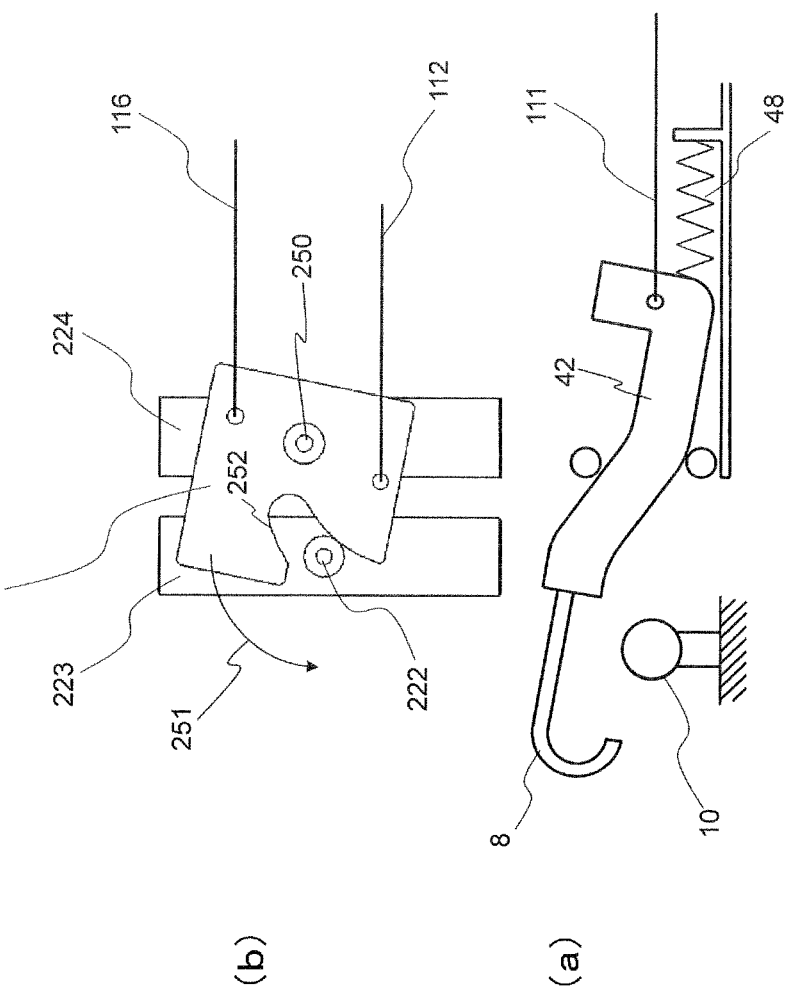
FIG. 28(a) is a simplified view showing the hook 8 of the docking unit 4, and a coupling bar 10 of the docking unit 5.
FIG. 28(b) is a simplified explanatory view showing an electric connector 224 and a coupling tool 221 of the docking unit 4, and an electric connector 223 and pins 222 of the docking unit 5.

Additionally, if the hook 8 and the coupling tools 221 are shown in a simplified manner, the hook and the coupling tools are in the state of FIGS. 28(a) and 28(b), and are not engaged with the coupling bar 10 and the pins 222.

Figure 29:
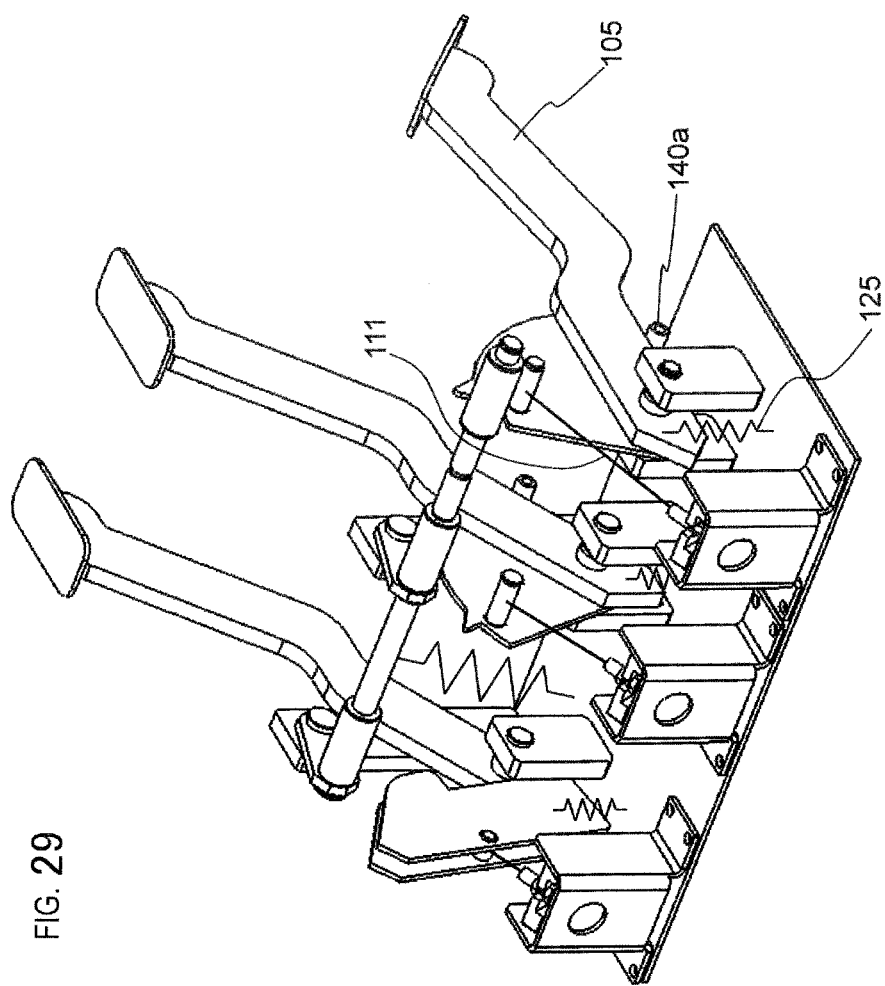
FIG. 29 is a perspective view of a state where a pedal 105 of the pedal unit is stepped on, and the locking plate A 108 is locked to a locking bar 115.
Figure 30:
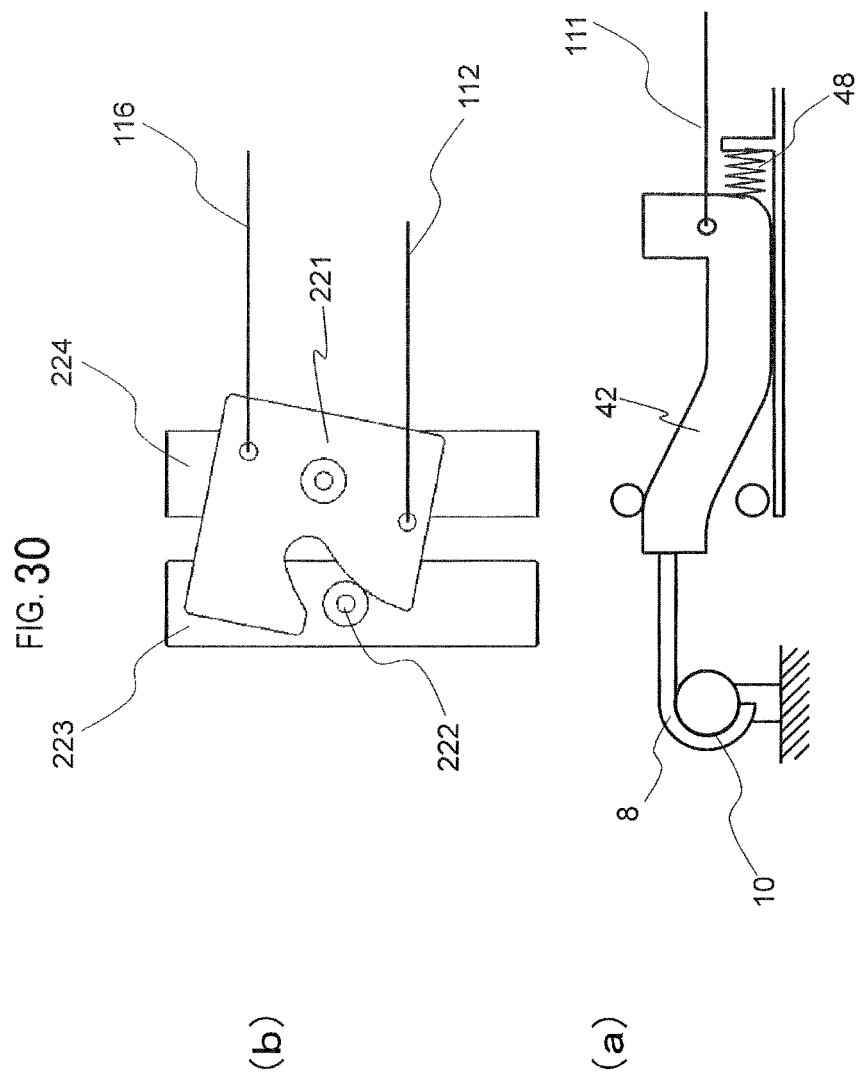
FIG. 30(a) is an explanatory view showing a state where the hook 8 is coupled to the coupling bar 10 through the operation of FIG. 29.
FIG. 30(b) is an explanatory view showing a state where the electric connector 224 and the coupling tool 221 are not coupled to the electric connector 223 and the pins 222 through the operation of FIG. 29.

In the pedal unit 104, first, the examiner steps on the mechanical docking pedal 105 as shown in FIG. 29 (Step 601 of FIG. 26). Through this operation, the pedal-receiving shaft 140a is pushed by the pedal 105, the locking plate A 108 rotates together with the pedal 105, and the ire A 111 is pulled. At this time, the locking bar 115 contacts the circular-arc region 108a of the locking plate A 108 with the radius r1. If the locking plate A 108 is rotated until the protrusion 143 comes to the position of the locking bar 115, and the locking plate A 108 is further rotated, the locking bar 115 rides over the protrusion 143 and the radius r2 (<r1) of the locking plate A 108 reaches the cutout region 108b. Unless the locking bar 15 is pushed up by the release plate 117, the locking bar 15 cannot return while riding over the steeply rising side surface shape of the protrusion 143, and the locking plate A 108 is locked by the locking bar 115 (Step 602). Accordingly, if the wire A 111 is pulled, the hook 8 of the docking unit 4 of the bed 3 is pulled and is coupled to the coupling bar 10 of the docking unit 5, and the docking units 4 and 5 are fixed (Step 603, FIG. 30(a)). Accordingly, the mechanical docking is completed. In addition, since the operation of the electrical docking is not performed yet at this time, the electric connectors 224 and 223 are not coupled together as shown in FIG. 30(b).

Figure 31:
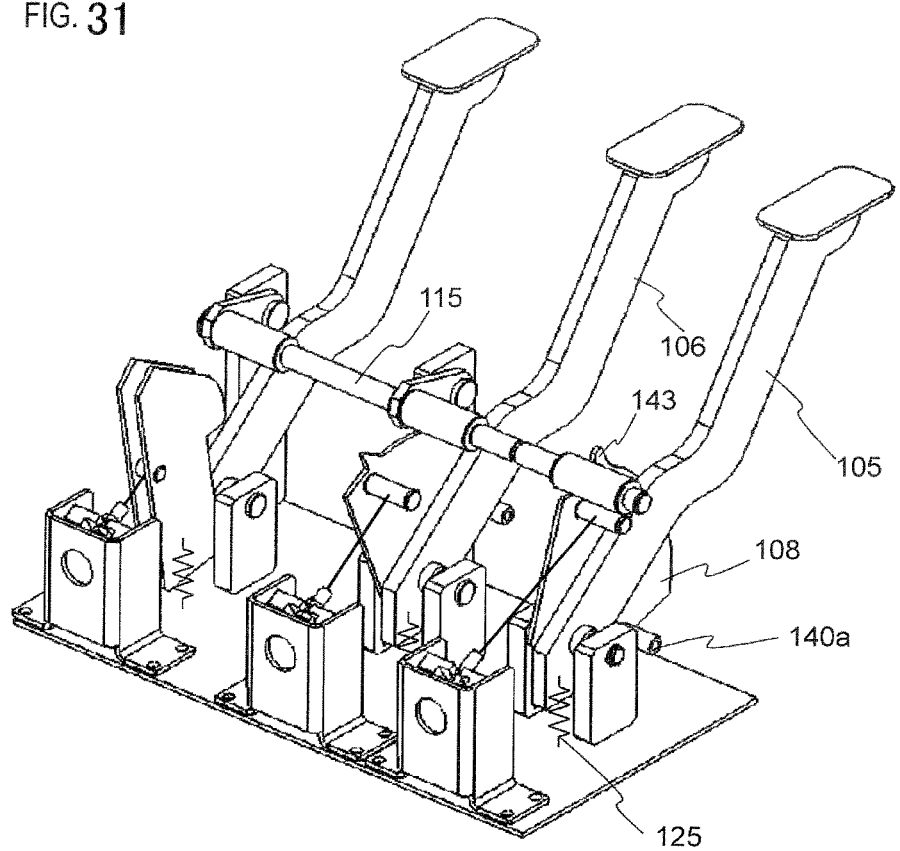
FIG. 31 is a perspective view of a state where only the pedal 105 returns to an initial position from the state of FIG. 29.

Next, if the operator lifts his/her foot off the mechanical docking pedal 105, only the mechanical docking pedal 105 returns to its initial position as shown in FIG. 31 by the force of the spring 125 for pedal return (Steps 604 and 605).

Through the above operation, the locking bar 115 reaches the cutout region 108b with the radius r2 (<r1), of the locking plate A 108, whereby the locking bar 115 also comes in contact with the circular-arc region 109a of the locking plate B 109 with the same radius r2. Hence, the locking plate B1 is brought into a state where the locking plate is lockable to locking bar 115.

Figure 32:
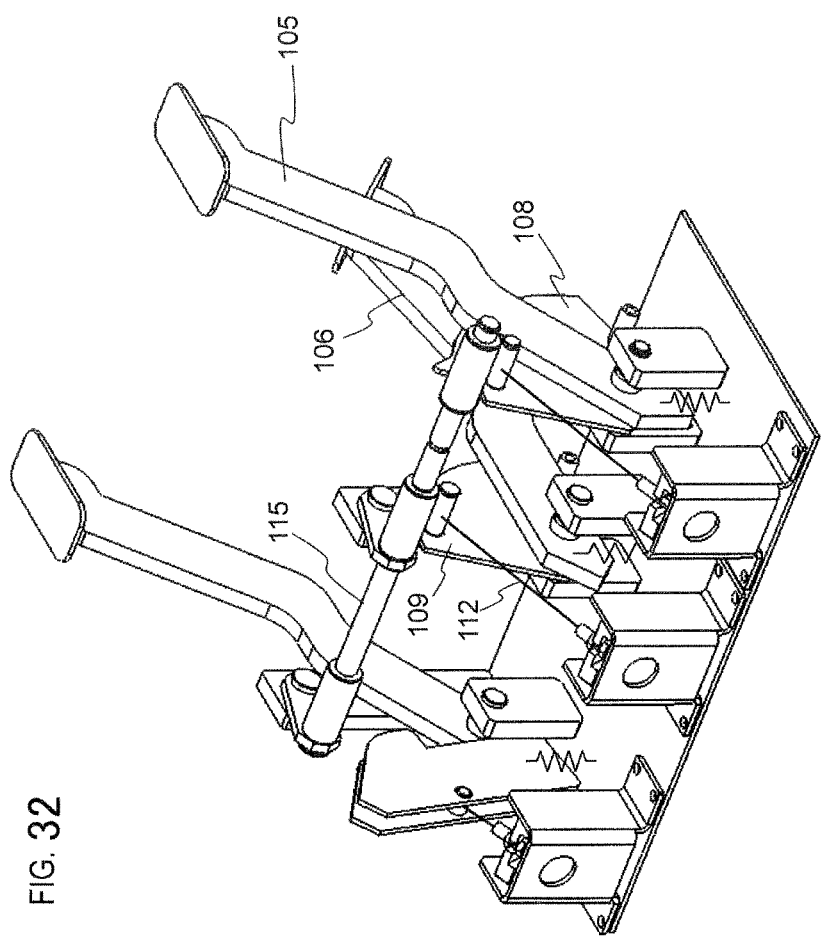
FIG. 32 is a perspective view of a state where a pedal 106 is stepped on from the state of FIG. 31 and the locking plate B 109 is locked.
Figure 33:
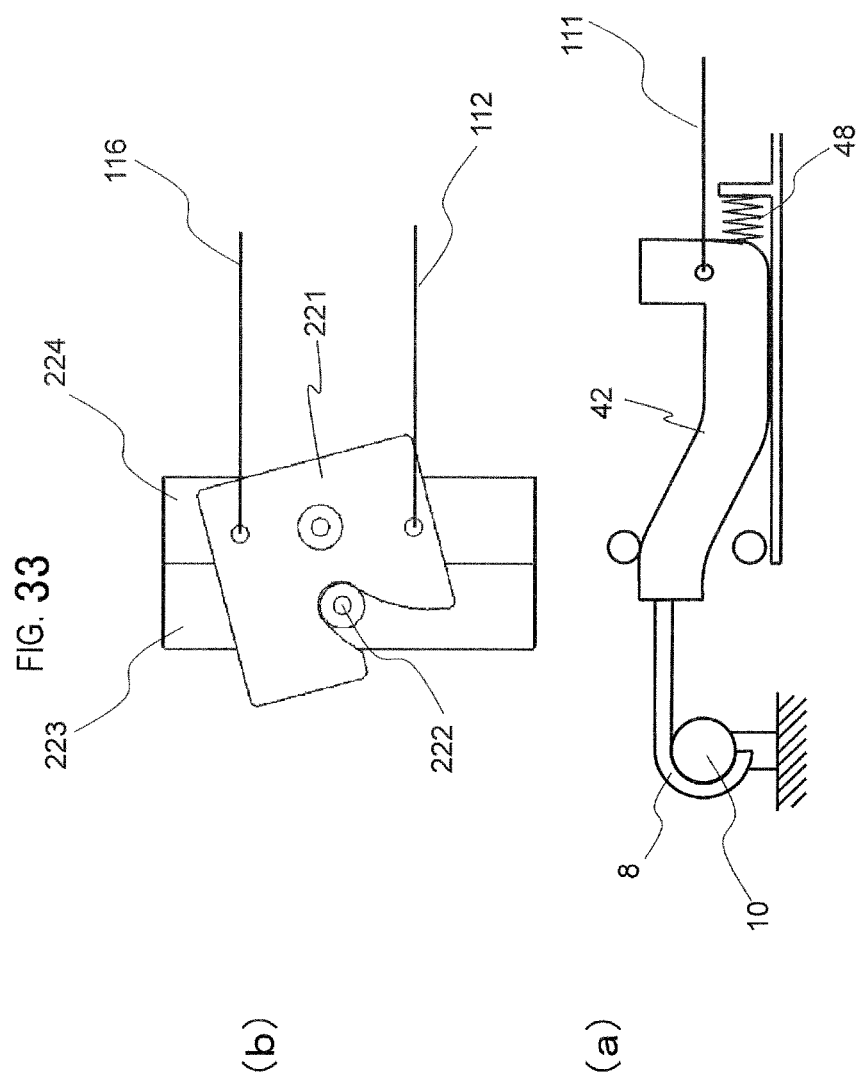
FIG. 33(a) is a view showing a state where the hook 8 is coupled to the coupling bar 10.
FIG. 33(b) is a view showing a state where the electric connector 224 of the docking unit 4 is coupled to the electric connector 223 of the docking unit 5 of the apparatus main body 2 by the coupling tools 221 through the operation of FIG. 32.

In this state, if the electrical docking pedal 106 is stepped on as shown in FIG. 32, the pedal-receiving shaft 141a is pushed by the pedal 106, the locking plate B 109 is rotated and the wire B 112 is pulled. At this time, the locking bar 115 contacts the circular-arc region 109a of the locking plate B 109 with the radius r2. Thus, if the locking plate B 109 rotated until the protrusion 144 comes to the position of the locking bar 115, and the locking plate B 109 is further rotated, the locking bar 115 rides over the protrusion 144 and reaches the locking region 109b. Unless the locking bar 15 is pushed up by the release plate 117, the locking bar cannot return while riding over the steeply rising side surface shape of the protrusion 144, and as shown in FIG. 32, the locking plate B 109 is locked by the locking bar 115 (Step 606). Since the radius of the locking region 109b of the locking plate 109 is r2 and is equal to the radius r2 of a region that contacts the locking bar 115 of the locking plate A 108 in a locked state, the locking bar 115 contacts the locking plate A 108 and the locking plate B 109 simultaneously, and is brought into a state where the locking bar locks both the locking plates (Step 607). If the wire B 112 is pulled with the rotation of the locking plate B 109, the coupling tools 221 are rotated to pull in the pins 22 as shown in FIG. 33(b). Accordingly, the electric connector 224 of the docking unit 4 on the bed 3 side and the electric connector 223 of the docking unit 5 on the apparatus main body 2 side are fitted to each other, and the electrical docking is completed (Step 608). At this time, since the hock 8 is already coupled to the coupling bar 10 in Step 603 as shown in FIG. 33(a), the docking units 4 and 5 are not only mechanically but also electrically coupled to each other.

Figure 34:
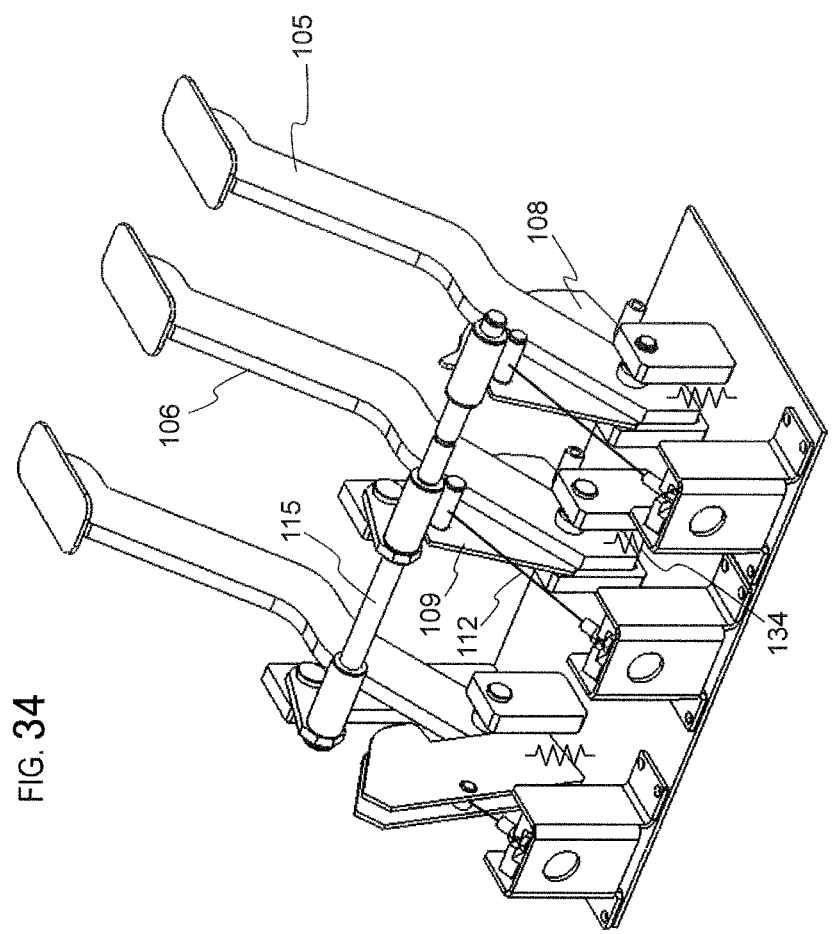
FIG. 34 is a perspective view of a state where only the pedal 106 returns to an initial position from the state of FIG. 32.

Next, if the operator lifts his/her foot off the electrical docking pedal 106, only the electrical docking pedal 106 returns to its initial position as shown in FIG. 34 by the force of the spring 134 for pedal return (Steps 609 and 610).

From the above, the mechanical docking and the electrical docking are performed in this order, and the docking is completed (Step 611).

In the above configuration, when the locking bar 115 rides over the protrusions 143 and 144 of the locking plate A 108 and locking plate B 109, a pedal operating force increases and decreases rapidly, and the examiner can obtain an operation feeling. Additionally, when the circular-arc region 108a with the radius r1, of the locking plate A 108 is located at its initial position, the locking bar 115 contacts the locking plate A 108, and the locking bar 115 does not contact the locking plate B 109 anywhere. That is, even the largest radius r5 of the protrusion 144 among the radius r4, r5, and r2 of the locking plate B 109 is smaller than the radius r1 of the locking plate A 108. For this reason, even if the examiner operates the electrical docking pedal 106, there is no operation feeling because the locking plate B 109 does not contact the locking bar 115 and the pedal can be comfortably stepped on with a small force. Accordingly, even if the electrical docking pedal 106 is stepped on in an unlocked state before operating the mechanical docking pedal 105, locking is not caused, the electrical docking cannot be performed, and the operator can notice an erroneous procedure from a difference in an operation feeling from that during a normal time.

Figure 35:
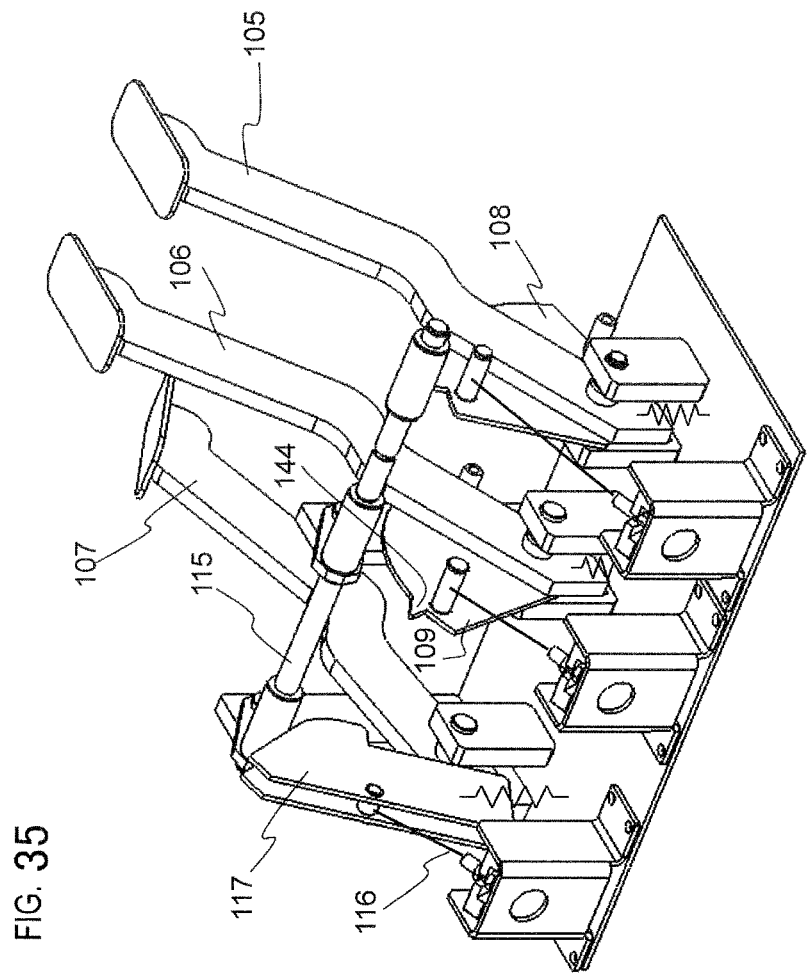
FIG. 35 is a perspective view of a state where the pedal 107 is shallowly stepped on from the state of FIG. 34, and the locking plate B 109 is unlocked.

Next, the flow of the docking release will be described with reference to FIG. 27. If the release pedal 107 is stepped on as shown in FIG. 35 in the above-described docking completion state (Step 611), the wire C 116 is pulled by the release plate 117, and the coupling tools 221 are pulled in a release direction (Step 701). The locking bar 115 is simultaneously gradually pushed up by the inclined surface of the tip portion of the release plate 117. Accordingly, if the height of the locking bar 115 reaches the radius r5 of the protrusion 144 of the locking plate B 109, the locking of the locking plate B 109 is first released as shown in FIG. 35 (Step 702).

Figure 36:
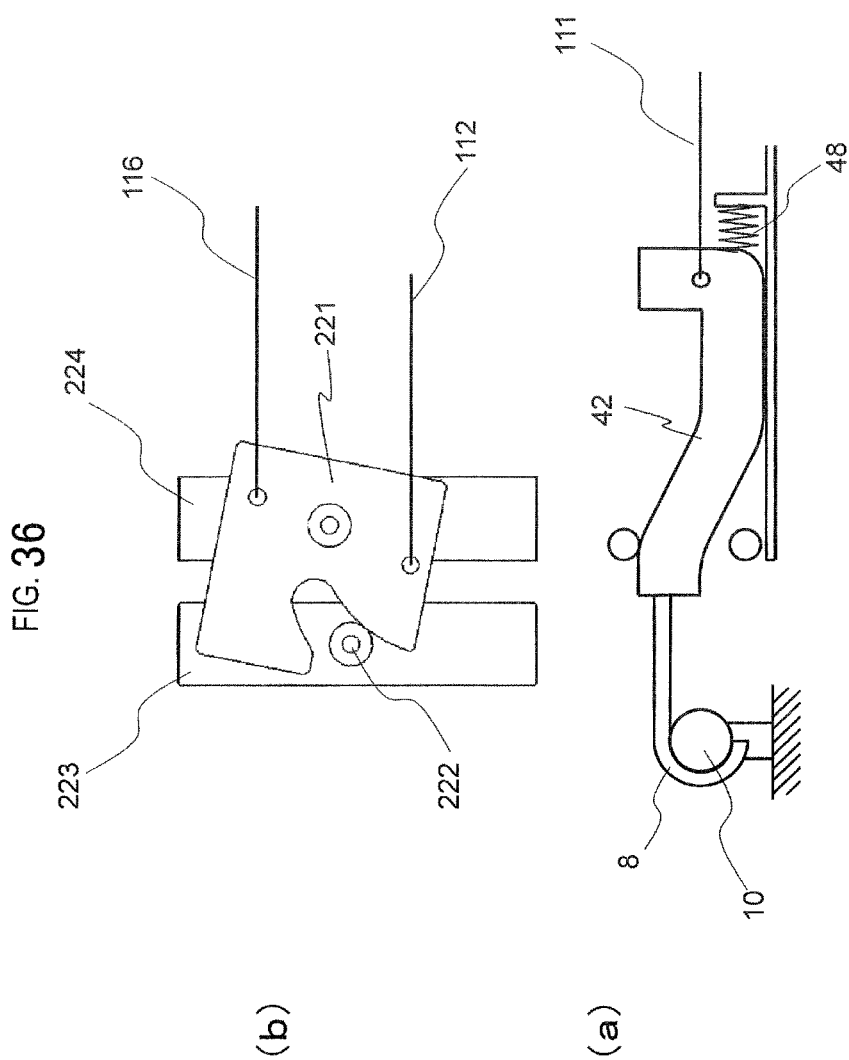
FIG. 36(a) is an explanatory view showing a state where the hook 8 is coupled to the coupling bar 10.
FIG. 36(b) is a view showing a state where the electric connector 224 is decoupled from the electric connector 223 through the operation of FIG. 35.

Accordingly, a force with which the locking plate B 109 pulls the wire B 112 is released and added to a force with which the wire C 116 pulls the coupling tools 221 in the release direction, and the coupling tools 221 rotate reversely as shown in FIG. 36(*b*) to push out the pin 222 and release the coupling between the electric connectors 223 and 224 (Step 703). The electrical docking is first released as described above. At this time, since the locking plate A 108 is still in the locked state, as shown in FIG. 36(*a*), the hook 8 remains coupled to the coupling bar 10.

Figure 37:
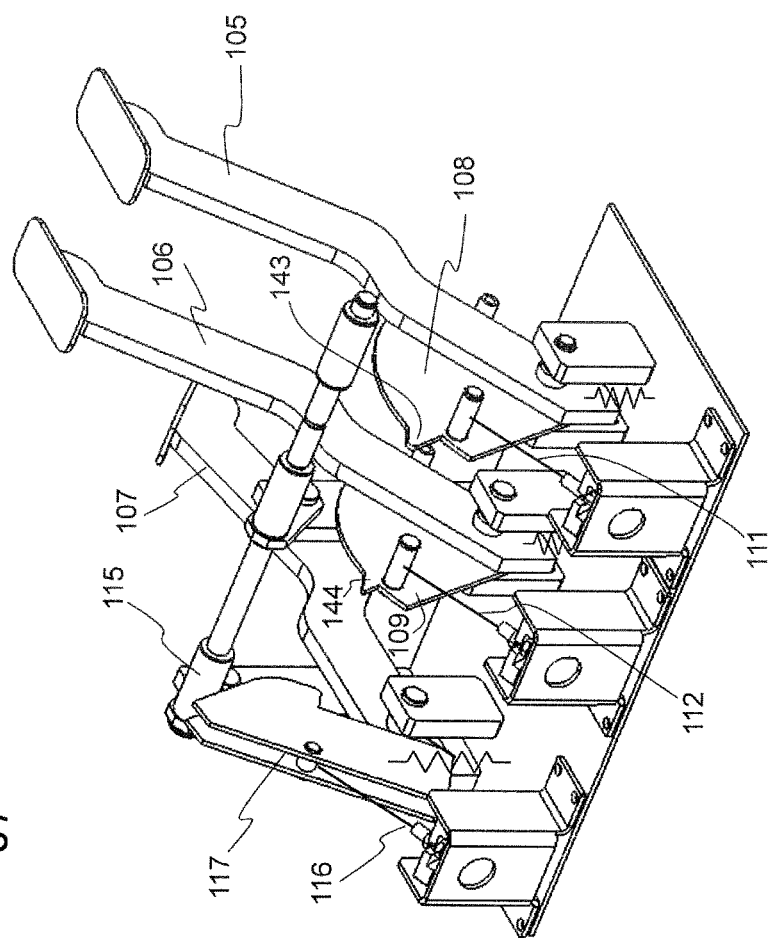
FIG. 37 is a perspective view of a state where the pedal 107 is deeply stepped on from the state of FIG. 35, and the locking plate A 108 is unlocked.
Figure 38:
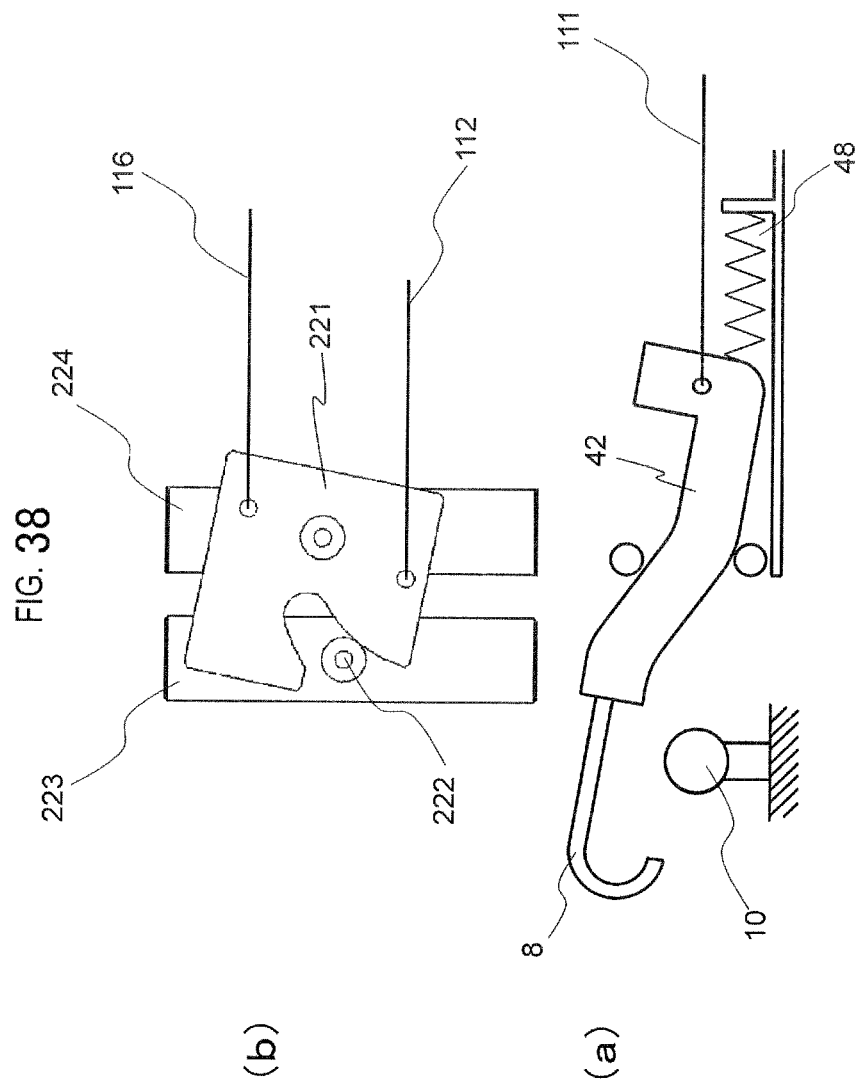
FIG. 38(a) is an explanatory view showing a state where the hook 8 is decoupled from the coupling bar 10 through the operation of FIG. 37.
FIG. 38(b) is an explanatory view showing a state where the electric connector 224 is decoupled from the electric connector 223 through the operation of FIG. 37.

If the examiner further steps on the release pedal 7 deeply as shown in FIG. 37 (Step 704), the release plate 117 further pushes up the locking bar 115, and if the height of the locking bar 115 reaches the height r3 of the tip of the protrusion 143 of the locking plate A, as shown in FIG. 37, the locking of the locking plate A 108 is released (Step 705). Accordingly, a force with which the locking plate A 108 pulls the wire A 111 is released, and the hook 8 is lifted by the force of the spring 48 arranged at the docking unit 4 as shown in FIG. 38(*a*), and returns to its initial state (Step 706). Accordingly, the hock 8 is removed from the coupling bar 10, and the mechanical docking is released. Simultaneously, since the wire A 111 is also pulled by the force of the spring 48 in a direction opposite to that during the docking operation, the locking plate A 108 also returns to its initial position. Since the electric connectors 223 and 224 are already decoupled as shown in FIG. 38 *b*) in Step 703, both the mechanical docking and the electrical docking are released in Step 703.

If the examiner lifts his/her foot from the release pedal 107, the release pedal 107 returns to its initial state by the pedal return spring 135 (FIG. 24) (Steps 707 to 709), which results in operation completion.

In this way, during release, the electrical docking is first released, and thereafter, the mechanical docking is released. From this, it is possible to avoid a state where the electric connectors 223 and 224 are coupled together in a state where the hook 8 is removed. Accordingly, it is possible to avoid an accident in which the bed 3 may move due to an unexpected operation during the coupling of the electric connectors 223 and 224, and the pins of the connectors may be damaged.

As described above, if the pedal unit 104 of the invention is not operated in determined order, locking is not caused, and the operation of an erroneous procedure can be prevented. Additionally, unless an examiner operates in the determined order, a pedal can be stepped on with a small force and an operation feeling is not obtained, either. Therefore, an operator can notice when an operating procedure is erroneous.

By using this pedal unit for the coupling between the bed and the apparatus main body, the mechanical docking and the electrical docking can be necessarily performed in this order, and damage of the electric connectors can be prevented. Additionally, during release, the release of the electrical docking and the release of the mechanical docking can be performed in this order, and a phenomenon in which the bed moves while the fitting of the electric connectors remains intact and damages to the connectors can be prevented.

Additionally, in the pedal unit of the invention, a pedal returns to its initial position if a foot is lifted from the pedal. Therefore, it is possible to prevent an accident in which, during release, the pedal returns to its initial position unexpectedly and collides with an operator's foot.

Figure 39:
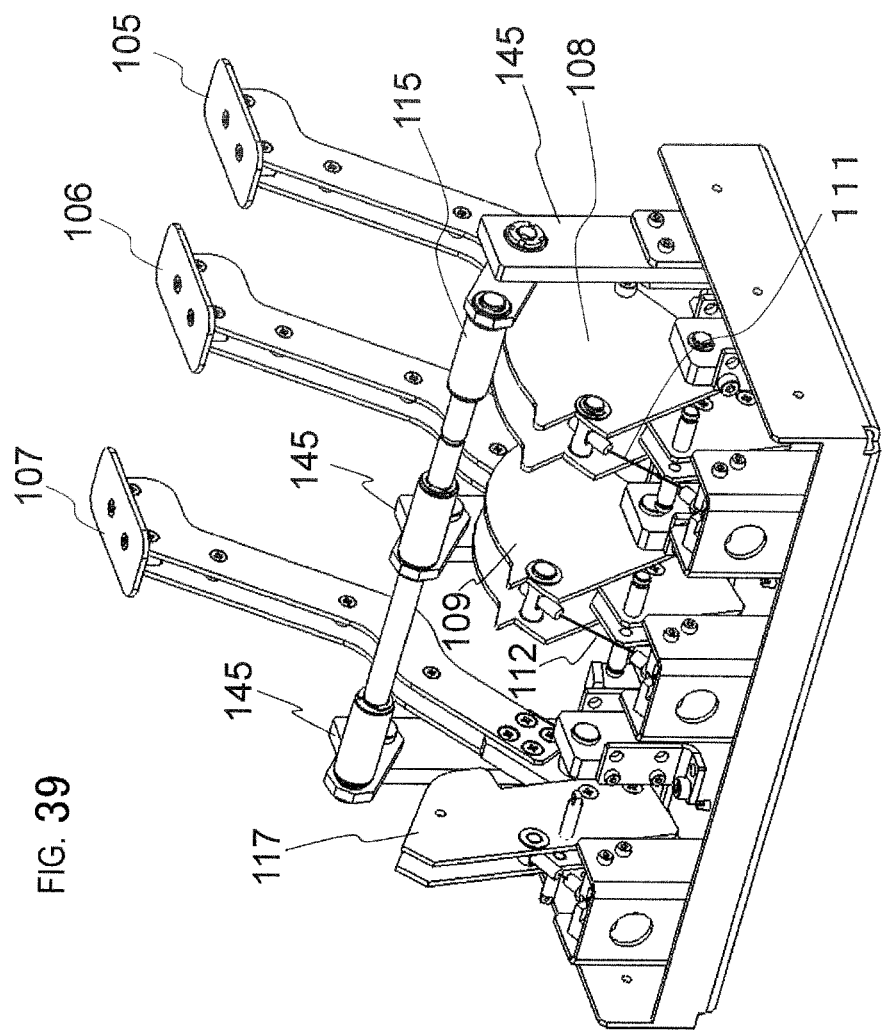
FIG. 39 is a perspective view of a configuration in which the pedal unit of the bed of the embodiments are partially changed.

In addition, the invention is not limited to the shape of FIG. 24, and the shape can be arbitrarily changed. For example, as shown in FIG. 39, it is also possible to form the locking plate A 108 and locking plate B 109 into a double structure to improve strength. Additionally, it is also possible to adopt a configuration in which the locking bar 115 is supported by the respective supporting portions 145 at both ends and the center thereof.

Additionally, the above-described embodiments provide the mechanism in which the pedals 105 and 106 that perform docking are two and are locked in two steps by two plates with different sizes. However, it is also possible to provide a mechanism where pedals that perform docking are three or more and are locked in three or more steps. In this case, three locking plates with different radii are sequentially used.

REFERENCE SIGNS LIST

1: MEDICAL IMAGING APPARATUS
2: APPARATUS MAIN BODY
3: BED
4: DOCKING UNIT
5: DOCKING UNIT
6: PEDAL
7: COUPLING PLATE
8: HOOK
9: ROLLER
10: COUPLING BAR
31: TOP PLATE
32: TOP PLATE HOLDING PORTION
33: WHEEL
34: FRAME
35: BELLOWS PORTION
42: ROOK SUPPORTING PORTION
43: PROTRUSION
44: SLIDE GUIDE
46: WIRE GUIDE
47: BAR
48: SPRING
50: ROLLER UNIT
105, 106, 107: PEDAL
111: WIRE A
221: COUPLING TOOL
222: PIN
223: ELECTRIC CONNECTOR
224: ELECTRIC CONNECTOR
260: FRAME PORTION
262: OUTER SLIDE FRAME
270: CONNECTOR SUPPORTING FRAME
271, 272: SLIDING PLATE

The invention claimed is:
1. A medical imaging apparatus comprising:
an apparatus main body equipped with an imaging function of an object;
a movable bed; and
coupling mechanisms arranged on an apparatus main body side and a bed side, respectively, in order to detachably couple the bed to the apparatus main body, wherein
one coupling mechanism either on the apparatus main body side or on the bed side includes a coupling plate, and the other coupling mechanism includes a holding member that holds the coupling plate, and
a first electric connector is mounted on the coupling plate, a second electric connector is mounted on the holding member, and an electric connector coupling mechanism that couples the first and second electric connectors is mounted on at least one of the coupling plate and the holding member in a state where the coupling plate is held by the holding member, wherein the electric connector coupling mechanism is configured to include a hook-shaped coupling tool attached to one of the first and second electric connectors, and a pin attached to the other, and as the coupling tool is engaged with the pin, the first and second connectors are coupled together, the coupling tool includes a first arm that rotates the coupling tool in a direction in which the coupling tool is engaged with the pin, and a second arm that rotates the coupling tool in a direction in which the coupling tool is decoupled from the pin, and one end of a first wire is connected to the first arm, one end of a second wire is connected to the second arm, and the other ends of the first and second wires are connected to first and second operating units, respectively.

2. The medical imaging apparatus according to claim 1, wherein the electric connector coupling mechanism includes a sliding mechanism that slidably holds one of the first and second electric connectors in a direction approaching the other when the coupling tool is engaged with the pin.

3. The medical imaging apparatus according to claim 2, wherein the electric connector coupling mechanism includes a biasing member that biases one of the first and second electric connectors in a direction along the sliding mechanism away from the other when the coupling tool is disengaged from the pin.

4. The medical imaging apparatus according to claim 1, wherein the electric connector coupling mechanism includes a movable mechanism that displaces one of the first and second electric connectors to the other so as to align the first and second electric connectors with each other.

5. The medical imaging apparatus according to claim 4, wherein the movable mechanism includes an elastic member that supports either of the first or second electric connectors so as to be displaceable in directions of two or more dimensions with respect to the other.

6. The medical imaging apparatus according to claim 5, wherein the movable mechanism includes one or more sliding plates, the elastic member supports the one or more sliding plates, and either of the first or second electric connectors is supported by a front surface of a first sliding plate of the sliding plates.

7. The medical imaging apparatus according to claim 1, wherein a guide mechanism that is displaced by the second wire while being guided in a movement direction of the second arm is provided between the second arm and the second wire.

8. The medical imaging apparatus according to claim 1, wherein the main apparatus body is a magnetic resonance imaging apparatus.

9. A medical imaging apparatus comprising:
an apparatus main body equipped with an imaging function of an object;
a movable bed; and
coupling mechanisms arranged on an apparatus main body side and a bed side, respectively, in order to detachably couple the bed to the apparatus main body, wherein
one coupling mechanism either on the apparatus main body side or on the bed side includes a coupling plate, and the other coupling mechanism includes a holding member that holds the coupling plate, and a first electric connector is mounted on the coupling plate, a second electric connector is mounted on the holding member, and an electric connector coupling mechanism that couples the first and second electric connectors is mounted on at least one of the coupling plate and the holding member in a state where the coupling plate is held by the holding member, wherein the electric connector coupling mechanism includes a movable mechanism that displaces one of the first and second electric connectors to the other so as to align the first and second electric connectors with each other, wherein the movable mechanism includes an elastic member that supports either of the first or second electric connectors so as to be displaceable in directions of two or more dimensions with respect to the other, wherein the movable mechanism includes one or more sliding plates, the elastic member supports the one or more sliding plates, and either of the first or second electric connectors is supported by a front surface of a first sliding plate of the sliding plates, and wherein the first sliding plate is supported by the elastic member from vertical and horizontal directions, and a second sliding plate arranged so as to contact a rear surface of the first sliding plate is supported by the elastic member so as to be pushed out from the rear surface to the front by the elastic member.

10. The medical imaging apparatus according to claim 9, wherein the movable mechanism includes a ball joint and the elastic member supports the ball joint.

11. The medical imaging apparatus according to claim 9, wherein one or more locating pins are formed on one of facing surfaces of the first and second electric connectors so as to protrude toward the other facing surface, and holes having the locating pins inserted thereinto are provided in the other facing surface.

12. The medical imaging apparatus according to claim 11, wherein
two or more locating pins are provided,
the first and second electric connectors are mounted on the coupling plate and the holding member so as to face each other with a predetermined spacing in a state where the coupling plate is held by the holding member, and
a long pin among the locating pins is longer than the predetermined spacing, and a short pin is shorter than the predetermined spacing.

13. A bed for a medical imaging apparatus that is attachable to and detachable from the medical imaging apparatus, and is movable, the bed comprising:
a coupling mechanism that is coupled to the medical imaging apparatus, wherein
the coupling mechanism includes a coupling plate having one end fixed and the other end protruding toward the medical imaging apparatus, and
an electric connector coupling mechanism that couples a first electric connector to a second electric connector arranged on a medical imaging apparatus side is mounted on the coupling plate, wherein the electric connector coupling mechanism is configured to include a hook-shaped coupling tool attached to one of the first and second electric connectors, and a pin attached to the other, and as the coupling tool is engaged with the pin, the first and second connectors are coupled together, the coupling tool includes a first arm that rotates the coupling tool in a direction in which the coupling tool is engaged with the pin, and a second arm that rotates the coupling tool in a direction in which the coupling tool is decoupled from the pin, and one end of a first wire is connected to the first arm, one end of a second wire is connected to the second arm, and the other ends of the first and second wires are connected to first and second operating units, respectively.

* * * * *